United States Patent
Rosenberg et al.

(10) Patent No.: US 8,195,292 B2
(45) Date of Patent: Jun. 5, 2012

(54) CARDIAC RESYNCHRONIZATION THERAPY OPTIMIZATION USING PARAMETER ESTIMATION FROM REALTIME ELECTRODE MOTION TRACKING

(75) Inventors: Stuart Rosenberg, Castaic, CA (US); Kjell Noren, Solna (SE); Kyungmoo Ryu, Palmdale, CA (US); Wenbo Hou, Lancaster, CA (US); Allen Keel, San Jose, CA (US); Michael Yang, Thousand Oaks, CA (US)

(73) Assignee: Pacestter, Inc., Sylmar, CA (US)

( * ) Notice: Subject to any disclaimer, the term of this patent is extended or adjusted under 35 U.S.C. 154(b) by 563 days.

(21) Appl. No.: 12/398,460

(22) Filed: Mar. 5, 2009

(65) Prior Publication Data
US 2009/0254140 A1    Oct. 8, 2009

Related U.S. Application Data

(63) Continuation-in-part of application No. 11/676,108, filed on Feb. 16, 2007.

(60) Provisional application No. 61/060,059, filed on Jun. 9, 2008.

(51) Int. Cl.
*A61N 1/00* (2006.01)
*A61B 5/04* (2006.01)

(52) U.S. Cl. ............. 607/9; 600/374; 600/509; 600/513

(58) Field of Classification Search ...... 607/9; 600/374, 600/509, 513
See application file for complete search history.

(56) References Cited

U.S. PATENT DOCUMENTS

| 4,712,555 | A | 12/1987 | Thornander et al. |
| 4,788,980 | A | 12/1988 | Mann et al. |
| 4,940,052 | A | 7/1990 | Mann et al. |
| 5,297,549 | A | 3/1994 | Beatty et al. |
| 5,466,254 | A | 11/1995 | Helland |
| 5,476,483 | A | 12/1995 | Bornzin et al. |
| 5,553,611 | A | 9/1996 | Budd et al. |
| 6,240,307 | B1 | 5/2001 | Beatty et al. |
| 6,314,323 | B1 | 11/2001 | Ekwall |
| 6,368,285 | B1 * | 4/2002 | Osadchy et al. .............. 600/508 |
| 6,885,889 | B2 | 4/2005 | Chinchoy |
| 6,947,785 | B1 | 9/2005 | Beatty et al. |
| 6,978,168 | B2 | 12/2005 | Beatty et al. |
| 7,613,500 | B2 | 11/2009 | Vass et al. |
| 2006/0161211 | A1 | 7/2006 | Thompson |

(Continued)

FOREIGN PATENT DOCUMENTS

WO    2006042039 A2    4/2006

(Continued)

OTHER PUBLICATIONS

GRAS, Daniel et al., "The selection of patients for cardiac resynchronization therapy," European Heart Journal Supplements (2004);Supplement D:D98-0100.

(Continued)

*Primary Examiner* — Nicole F Lavert

(57) ABSTRACT

An exemplary method includes providing at least two-dimensional position information, for at least two points in time, for an electrode located in a cardiac space; determining a local estimator based on the position information; and, based at least in part on the determined local estimator, selecting a configuration for delivering a cardiac pacing therapy or diagnosing a cardiac condition. Exemplary methods for regional estimators and exemplary methods for global estimators are also disclosed along with devices and systems configured to perform various methods.

28 Claims, 16 Drawing Sheets

U.S. PATENT DOCUMENTS

| | | |
|---|---|---|
| 2006/0178586 A1 | 8/2006 | Dobak, III |
| 2006/0178589 A1 | 8/2006 | Dobak, III |
| 2007/0135721 A1 | 6/2007 | Zdeblick |
| 2007/0167758 A1 | 7/2007 | Costello |
| 2008/0058656 A1 | 3/2008 | Costello et al. |
| 2008/0183072 A1 | 7/2008 | Robertson et al. |
| 2009/0093857 A1 | 4/2009 | Markowitz et al. |

FOREIGN PATENT DOCUMENTS

| | | |
|---|---|---|
| WO | 2006105474 A2 | 10/2006 |
| WO | 2006105474 A3 | 10/2006 |
| WO | 2007111542 A1 | 10/2007 |
| WO | 2007120290 A2 | 10/2007 |
| WO | 2007120290 A3 | 10/2007 |

OTHER PUBLICATIONS

Kadish, Alan MD et al., "Mapping of Atrial Activation With a Noncontact, Multielectrode Catheter in Dogs," Circulation. 1999; 99:1906-1913.

Klemm, Hanno U. MD et al., "Simultaneous mapping of activation and motion timing in the healthy and chronically ischemic heart," Heart Rhythm 2006;3:781-788.

Paul, Thomas MD et al., "Atrial Reentrant Tachycardia After Surgery for Congenital Heart Disease. Endocardial Mapping and Radiofrequency Catheter Ablation Using a Novel, Noncontact Mapping System," Circulation. 2001;103:2266-2271.

* cited by examiner

CARDIAC RESYNCHRONIZATION THERAPY OPTIMIZATION USING PARAMETER ESTIMATION FROM REALTIME ELECTRODE MOTION TRACKING

RELATED APPLICATIONS

This patent application claims the benefit of U.S. Provisional Patent Application Ser. No. 61/060,059, entitled "Cardiac Resynchronization Therapy Optimization Using Volume Parameter Estimation from Real-time Electrode Motion Tracking," filed on Jun. 9, 2008, and is a continuation-in-part of U.S. application Ser. No. 11/676,108, entitled "Motion-based Optimization of Cardiac Stimulation Therapy," filed on Feb. 16, 2007 both of which are incorporated by reference herein.

TECHNICAL FIELD

Subject matter presented herein relates generally to cardiac pacing and/or stimulation therapy. Various examples concern analysis of mechanical information for optimizing such therapies, monitoring patient condition, monitoring device condition and the like.

BACKGROUND

Cardiac resynchronization therapy (CRT) aims to improve cardiac performance by synchronizing the ventricles. While the term "synchronization" is used, for some patients, a delay between contraction of the right ventricle and the left ventricle may be optimal. Hence, the term synchronization refers more generally to ventricular timing that improves cardiac performance. A general objective measure of lack of synchrony or dysynchrony is QRS width representative of contraction of both ventricles. For example, a QRS width greater than about 130 ms may indicate dysynchrony.

CRT can improve a variety of cardiac performance measures including left ventricular mechanical function, cardiac index, decreased pulmonary artery pressures, decrease in myocardial oxygen consumption, decrease in dynamic mitral regurgitation, increase in global ejection fraction, decrease in NYHA class, increased quality of life scores, increased distance covered during a 6-minute walk test, etc. Effects such as reverse modeling may also be seen, for example, three to six months after initiating CRT. Patients that show such improvements are classified as CRT "responders". However, for a variety of reasons, not all patients respond to CRT. For example, if a left ventricular stimulation lead cannot locate an electrode in a favorable position, then a patient may not respond to CRT.

Conventional placement criteria for a stimulation electrode typically focus on the location of latest electrical activation over the left ventricle. However, ischemic cardiomyopathy can cause non-uniform propagation of electrical activity over the myocardium. Thus, a site of latest electrical activation may not be optimal. In particular, such a site may be a poor candidate for maximizing cardiac stroke volume.

As described herein, various exemplary technologies allow a clinician, a system, etc., to optimize configuration of an implantable cardiac therapy device. In particular, various techniques include use of cardiac mechanical information to determine one or more local, regional or global estimator, which can indicate better configurations and can improve diagnosis of cardiac conditions.

SUMMARY

An exemplary method includes providing at least two-dimensional position information, for at least two points in time, for an electrode located in a cardiac space; determining a local estimator based on the position information; and, based at least in part on the determined local estimator, selecting a configuration for delivering a cardiac pacing therapy or diagnosing a cardiac condition. Exemplary methods for regional estimators and exemplary methods for global estimators are also disclosed along with devices and systems configured to perform various methods.

BRIEF DESCRIPTION OF THE DRAWINGS

Features and advantages of the described implementations can be more readily understood by reference to the following description taken in conjunction with the accompanying drawings.

DETAILED DESCRIPTION

Figure 1:
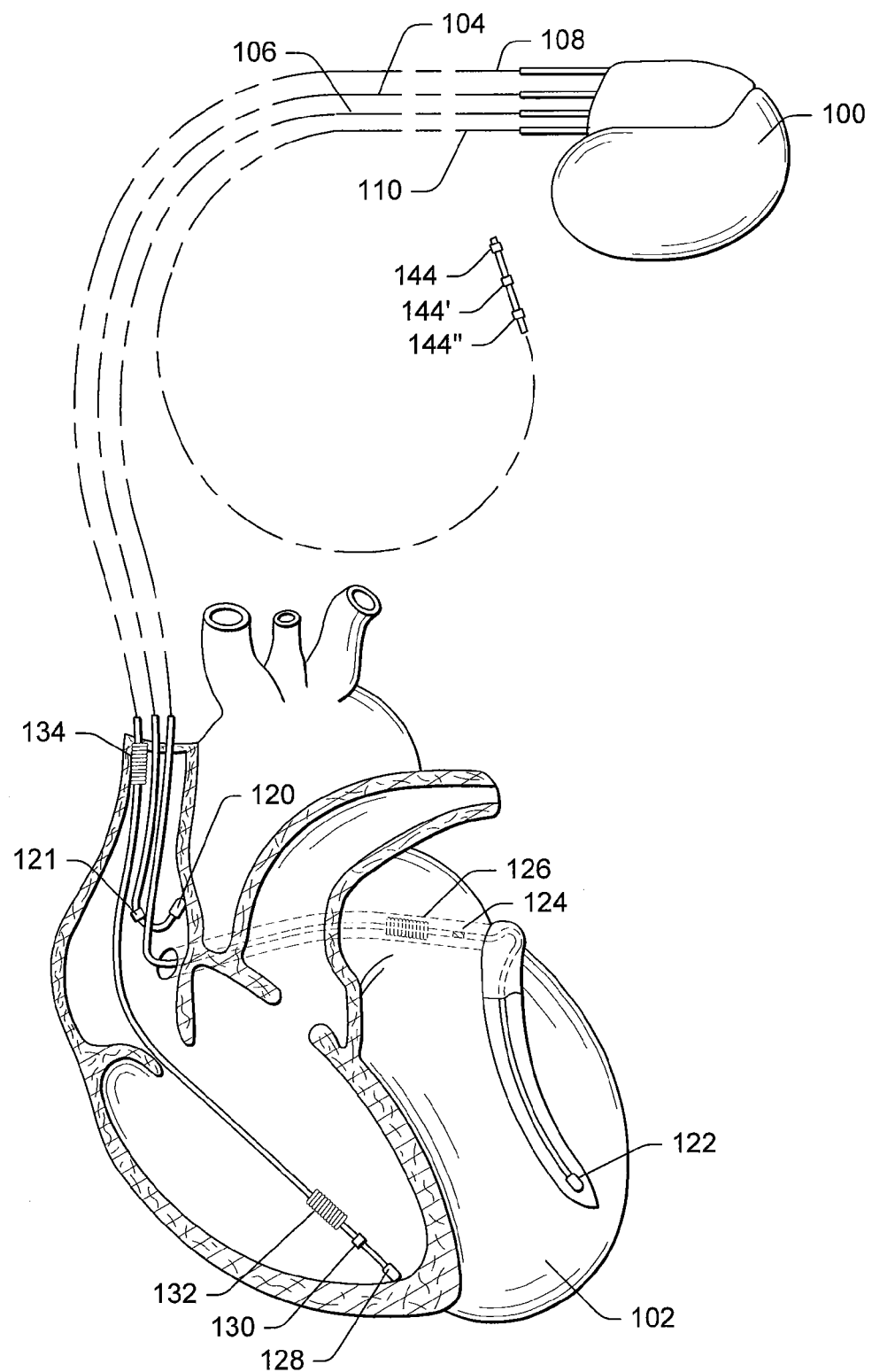
FIG. 1 is a simplified diagram illustrating an exemplary implantable stimulation device in electrical communication with at least three leads implanted into a patient's heart and at least one other lead for sensing and/or delivering stimulation and/or shock therapy. Other devices with more or fewer leads may also be suitable.

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Various exemplary methods, devices, systems, etc., rely on mechanical information to optimize cardiac stimulation therapy, to monitor patient condition, to monitor implantable device condition, or to more fully understand cardiac health. As described herein, various techniques acquire information about cardiac mechanics, referred to herein as mechanical information (e.g., position information with respect to one or more points in time, motion information, etc.). For example, an exemplary method includes positioning a plurality of electrodes in or on the heart, acquiring mechanical information by tracking positions of the electrodes during at least part of a cardiac cycle. Such electrodes may be associated with a catheter for temporary placement, a lead for chronic implantation or a combination of both.

Position tracking of an electrode or electrodes may be achieved in any of a variety of manners. For example, electrode patches may be placed on a patient's body to define a coordinate system (e.g., 1D, 2D, 3D, etc.) and to aid in acquisition of position and motion information for one or more implanted electrodes (e.g., due to cardiac mechanics). An implanted electrode may be positioned via a vessel (e.g., a vein) or via the pericardium (e.g., intrapericardial access to an epicardial location). An implanted electrode may be used to deliver stimulation energy from a particular stimulation site and where multiple electrodes are implanted, various stimulation sites may be tested.

In various examples, electrical information may be acquired as well and optionally used for gating acquisition of mechanical information or other purposes. Electrical activity may be measured using conventional techniques such as those for acquiring surface electrocardiograms or in vivo electrocardiograms (e.g., intracardiac electrograms). As described herein, the term "electrogram" (EGM) includes surface electrogram (ECG) and intracardiac electrogram (IEGM) as well as other types of electrograms that rely on one or more implanted electrodes.

Mechanical information may be analyzed with respect to stimulation energy delivered using one or more stimulation sites. An analysis of such information may be used to determine an optimal stimulation site or sites or, more generally, an optimal configuration. As described herein, a "configuration" can account for more than electrode placement or location as one or more stimulation parameters and/or stimulation timings (e.g., interelectrode timings) may be part of a "configuration".

An exemplary stimulation device is described followed by various techniques for acquiring and analyzing mechanical information. Various examples describe methods to determine a local estimate (or estimator or parameter), a regional estimate (or estimator or parameter) and a global estimate (or estimator or parameter). An exemplary program can optionally perform post-processing of information (e.g., mechanical information) and be configured for programming an implantable device capable of delivering cardiac resynchronization therapy (CRT).

Exemplary Stimulation Device

The techniques described below are intended to be implemented in connection with any stimulation device that is configured or configurable to delivery cardiac therapy and/or sense information germane to cardiac therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of nerves or other tissue. In addition, the device 100 includes a fourth lead 110 having, in this implementation, three electrodes 144, 144', 144" suitable for stimulation and/or sensing of physiologic signals. This lead may be positioned in and/or near a patient's heart and/or remote from the heart.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation and/or sensing.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of nerves or other tissue. Such a lead may include bifurcations or legs. For example, an exemplary coronary sinus lead includes pacing electrodes capable of delivering pacing pulses to a patient's left ventricle and at least one electrode capable of stimulating an autonomic nerve.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead.

Figure 2:
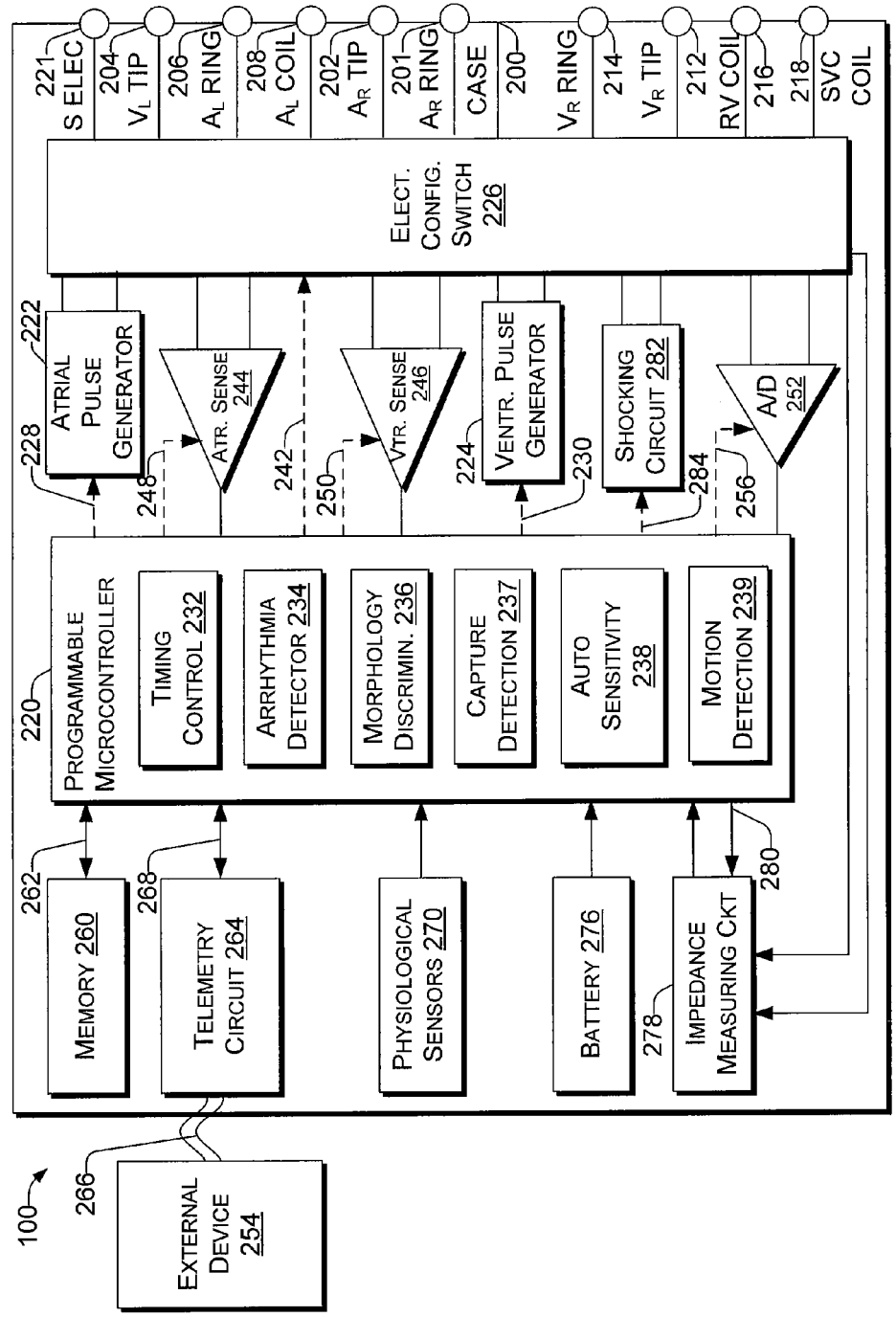
FIG. 2 is a functional block diagram of an exemplary implantable stimulation device illustrating basic elements that are configured to provide cardioversion, defibrillation, pacing stimulation and/or other tissue stimulation. The implantable stimulation device is further configured to sense information and administer therapy responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques, methods, etc., described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart.

Housing 200 for the stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking or other purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or other stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing. For example, electrodes of the lead 110 may connect to the device 100 at the terminal 221 or optionally at one or more other terminals.

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac or other therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052, the state-machine of U.S. Pat. Nos. 4,712,555 and 4,944,298, all of which are incorporated by reference herein. For a more detailed description of the various timing intervals used within the stimulation device and their inter-relationship, see U.S. Pat. No. 4,788,980, also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (AA) delay, or interventricular conduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation. The capture detection module 237, as described herein, may aid in acquisition, analysis, etc., of information relating to IEGMs and, in particular, act to distinguish capture versus non-capture versus fusion.

The microcontroller 220 further includes an optional motion module 239. The module 239 may be used for purposes of acquiring motion information, for example, in conjunction with a device (internal or external) that may use body surface patches or other electrodes (internal or external). The microcontroller 220 may initiate one or more algorithms of the module 239 in response to a signal detected by various circuitry or information received via the telemetry circuit 264. Instructions of the module 239 may cause the device 100 to measure potentials using one or more electrode configurations where the potentials correspond to a potential field generated by current delivered to the body using, for example, surface patch electrodes. Such a module may help monitor cardiac mechanics in relationship to cardiac electrical activity and may help to optimize cardiac resynchronization therapy. The module 239 may operate in conjunction with various other modules and/or circuits of the device 100 (e.g., the impedance measuring circuit 278, the switch 226, the A/D 252, etc.).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial and ventricular sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation which are sometimes referred to as "F-waves") and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Figure 11:
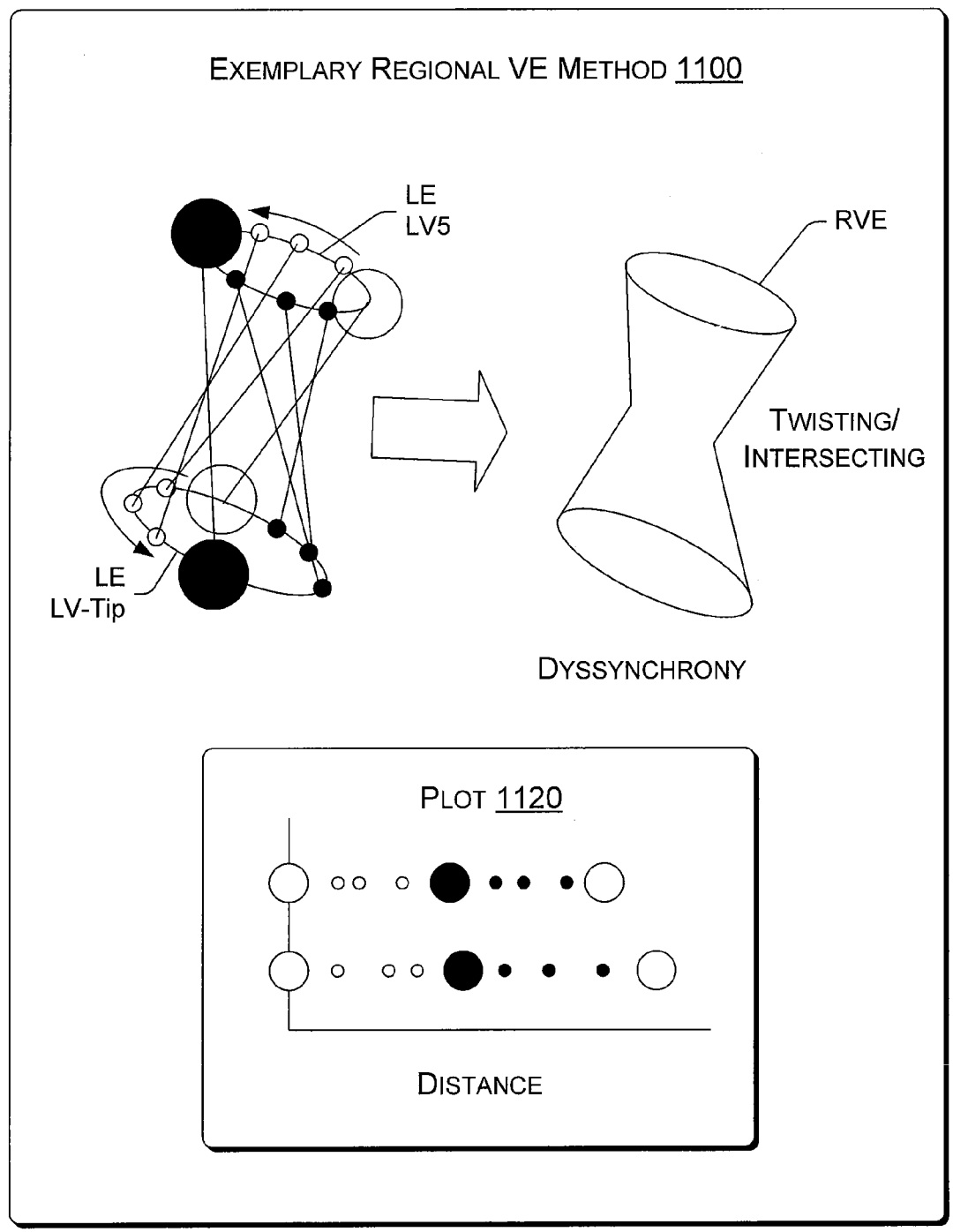
FIG. 11 is a diagram illustrating an exemplary method along with data plots that can indicate dysynchrony.

Cardiac signals are also applied to inputs of an analog-to-digital (A/D) data acquisition system 252. Additional configurations are shown in FIG. 11 and described further below. The data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes. A control signal 256 from the microcontroller 220 may instruct the A/D 252 to operate in a particular mode (e.g., resolution, amplification, etc.).

Various exemplary mechanisms for signal acquisition are described herein that optionally include use of one or more analog-to-digital converter. Various exemplary mechanisms allow for adjustment of one or more parameter associated with signal acquisition.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the device 100, etc., as contained in the microcontroller 220 or memory 260) to be sent to the external device 254 through an established communication link 266.

The stimulation device 100 can further include one or more physiologic sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 which is hereby incorporated by reference.

The one or more physiological sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As already mentioned, the implantable device 100 includes impedance measurement circuitry 278. Such a circuit may measure impedance or electrical resistance through use of various techniques. For example, the device 100 may deliver a low voltage (e.g., about 10 mV to about 20 mV) of alternating current between the RV tip electrode 128 and the case electrode 200. During delivery of this energy, the device 100 may measure resistance between these two electrodes where the resistance depends on any of a variety of factors. For example, the resistance may vary inversely with respect to volume of blood along the path.

In another example, resistance measurement occurs through use of a four terminal or electrode technique. For example, the exemplary device 100 may deliver an alternating current between one of the RV tip electrode 128 and the case electrode 200. During delivery, the device 100 may measure a potential between the RA ring electrode 121 and the RV ring electrode 130 where the potential is proportional to the resistance between the selected potential measurement electrodes.

With respect to two terminal or electrode techniques, where two electrodes are used to introduce current and the same two electrodes are used to measure potential, parasitic electrode-electrolyte impedances can introduce noise, especially at low current frequencies; thus, a greater number of terminals or electrodes may be used. For example, aforementioned four electrode techniques, where one electrode pair introduces current and another electrode pair measures potential, can cancel noise due to electrode-electrolyte interface impedance. Alternatively, where suitable or desirable, a two terminal or electrode technique may use larger electrode areas (e.g., even exceeding about 1 $cm^2$) and/or higher current frequencies (e.g., above about 10 kHz) to reduce noise.

Figure 3:
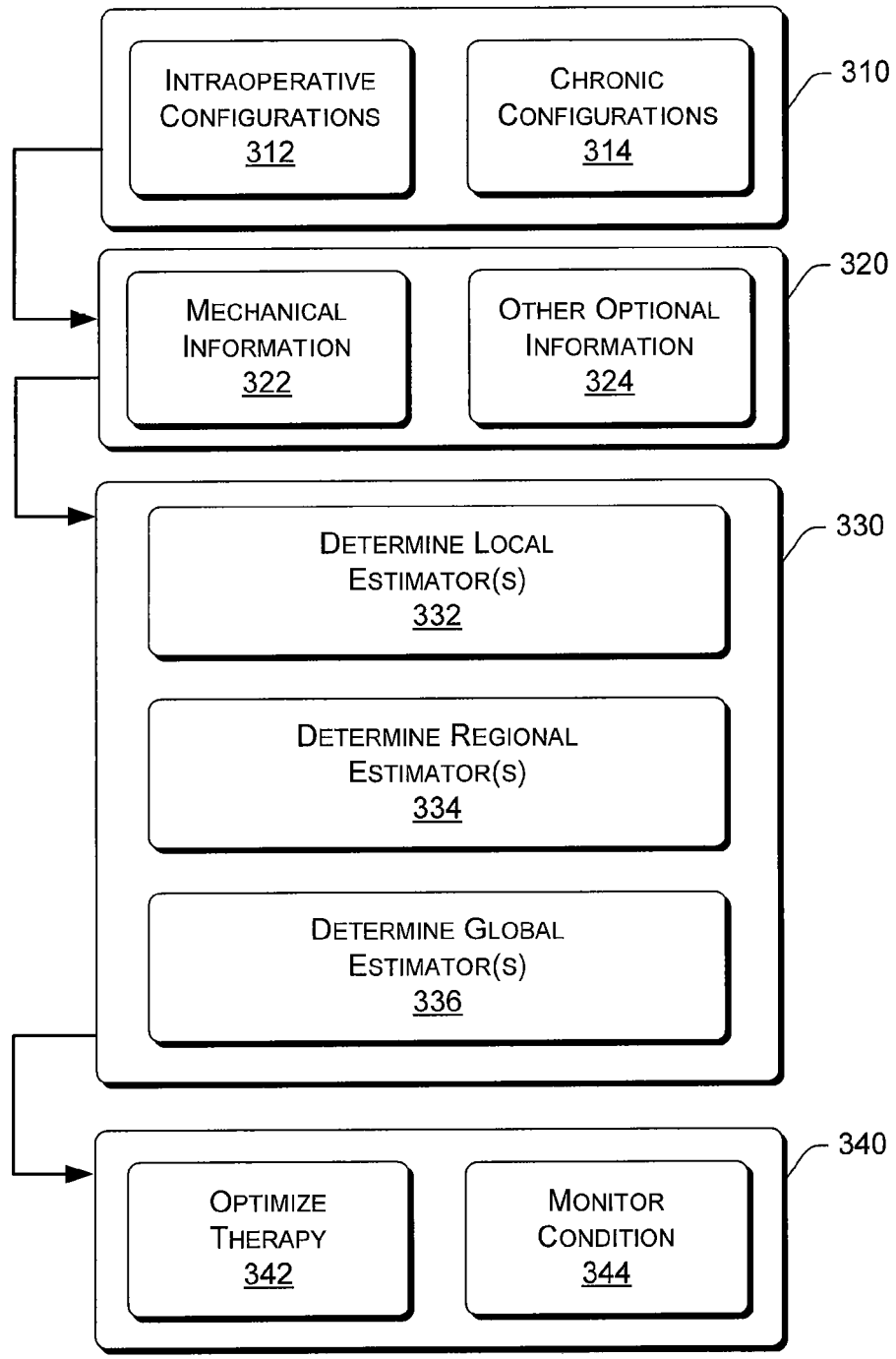
FIG. 3 is a block diagram of an exemplary method for optimizing therapy and/or monitoring conditions based at least in part on mechanical information.

FIG. 3 shows an exemplary method 300 for acquiring and analyzing mechanical information. In the example of FIG. 3, the method 300 includes a configurations block 310 that includes intraoperative configurations 312 and chronic configurations 314. The intraoperative configurations 312 pertain to configurations that may be achieved during an operative procedure. For example, during an operative procedure, one or more leads may be positioned in a patient where the one or more leads are connected to, or variously connectable to, a device configured to acquire information and optionally to deliver electrical energy to the patient (e.g., to the heart, to a nerve, to other tissue, etc.). The chronic configurations 314 pertain to configurations achievable by a chronically implanted device and its associated lead or leads. In general, intraoperative configurations include those achievable by physically re-positioning a lead in a patient's body while chronic configurations normally do not allow for re-positioning as a lead or leads are usually anchored during implantation or become anchored in the weeks to months after implantation. Chronic configurations do, however, include selection of a subset of the multiple implanted electrodes, for example using the tip electrode versus the first ring electrode as a cathode or using the tip and first ring as a bipolar pair versus using the tip and ring as two independent cathodes. Thus, intraoperative configurations include configurations available by changing device settings, electrode selection, and physical position of electrodes, while chronic configurations include only those configurations available by changing device settings and electrode selection, or "electronic repositioning" of one or more stimulation electrodes.

As indicated in FIG. 3, an acquisition block 320 includes acquisition of mechanical information 322 and optionally acquisition of other information 324 (e.g., electrical information as to electrical activity of the heart, biosensor information, etc.). While an arrow indicates that a relationship or relationships may exist between the configurations block 310 and the acquisition block 320, acquisition of information may occur by using in part an electrode (or other equipment) that is not part of a configuration. For example, the acquisition block 320 may rely on one or more surface electrodes that define a coordinate system or location system for locating an electrode that defines one or more configurations. For example, three pairs of surface electrodes positioned on a patient may be configured to deliver current and define a three-dimensional space whereby measurement of a potential locates an electrode in the three-dimensional space.

As described herein, an electrode may be configured for delivery of energy to the heart; for acquisition of electrical information; for acquisition of mechanical information; for acquisition of electrical information and mechanical information; for delivery of energy to the heart and for acquisition of electrical information; for delivery of energy to the heart and for acquisition of mechanical information; for delivery of energy to the heart, for acquisition of electrical information and for acquisition of mechanical information.

In various examples, acquisition of mechanical information occurs by measuring one or more potentials where the measuring relies on an electrode that may also be configured to deliver energy to the heart (e.g., electrical energy to pace a chamber of the heart). In such a scenario, the electrode may deliver energy sufficient to stimulate the heart and then be tracked along one or more dimensions to monitor the mechanical consequences of the stimulation. Further, such an electrode may be used to acquire electrical information (e.g., an IEGM that evidences an evoked response). Such an electrode can perform all three of these tasks with proper circuitry and control. For example, after delivery of the energy, the electrode may be configured for acquiring one or more potentials related to location and for acquiring an electrogram. To acquire potentials and an electrogram, circuitry may include gating or other sampling techniques (e.g., to avoid circuitry or interference issues). Such circuitry may rely on one sampling frequency for acquiring potentials for motion tracking and another sampling frequency for acquiring an electrogram.

The method 300 of FIG. 3 includes a determination block 330 for determining one or more volume estimators. The block 340 can determine local estimators (LEs) 332, regional estimators (REs) 334, global estimators (GEs) 336 or other custom estimators. For example, a LE may be determined based on a path swept by an electrode during a cardiac cycle or a portion thereof. In such an example, an electroanatomic mapping or locating system may acquire position information for an electrode at a set sampling rate (e.g., over at least a portion of a cardiac cycle) to thereby generate a path for the electrode with respect to time. In another example, a LE may be determined by two position points such as an end diastolic (ED) position point and an end systolic (ES) position point. In this example, the points may be selected to represent an expected maximum excursion of an electrode with respect to mechanical activity of the heart. As discussed further below, techniques to compensate for, or minimize, respiratory motion may be implemented; noting that cardiac performance with respect to respiratory motion or respiration (e.g., whether normal or abnormal) may also be examined based at least in part on the acquisition of mechanical information 322.

As inferred, a LE is based on movement of a point (e.g., a single electrode, a closely spaced electrode pair, etc.) where mechanical information 322 is acquired for the point. In contrast, a RE is based on movement of at least two points (e.g., two spaced electrodes along a common lead) where mechanical information 322 is acquired for each the points. With two or more points, a region can be defined and associated with tissue (e.g., a tissue volume).

A GE is based on movement of multiple points. For example, a method may acquire mechanical information for two electrodes of a left ventricular lead and acquire mechanical information for two electrodes of a right ventricular lead. In this example, a RE may be determined for the left ventricle and a RE may be determined for the right ventricle. As described herein, a GE may be based on two REs or the underlying position information for the two REs. Various other techniques exist to determine a GE, which are explained further below.

As shown in the example of FIG. 3, the conclusion block 340 may perform actions such as to optimize therapy 342 and/or to monitor patient and/or device condition 344. These options are described in more detail with respect to FIG. 4.

Figure 4:
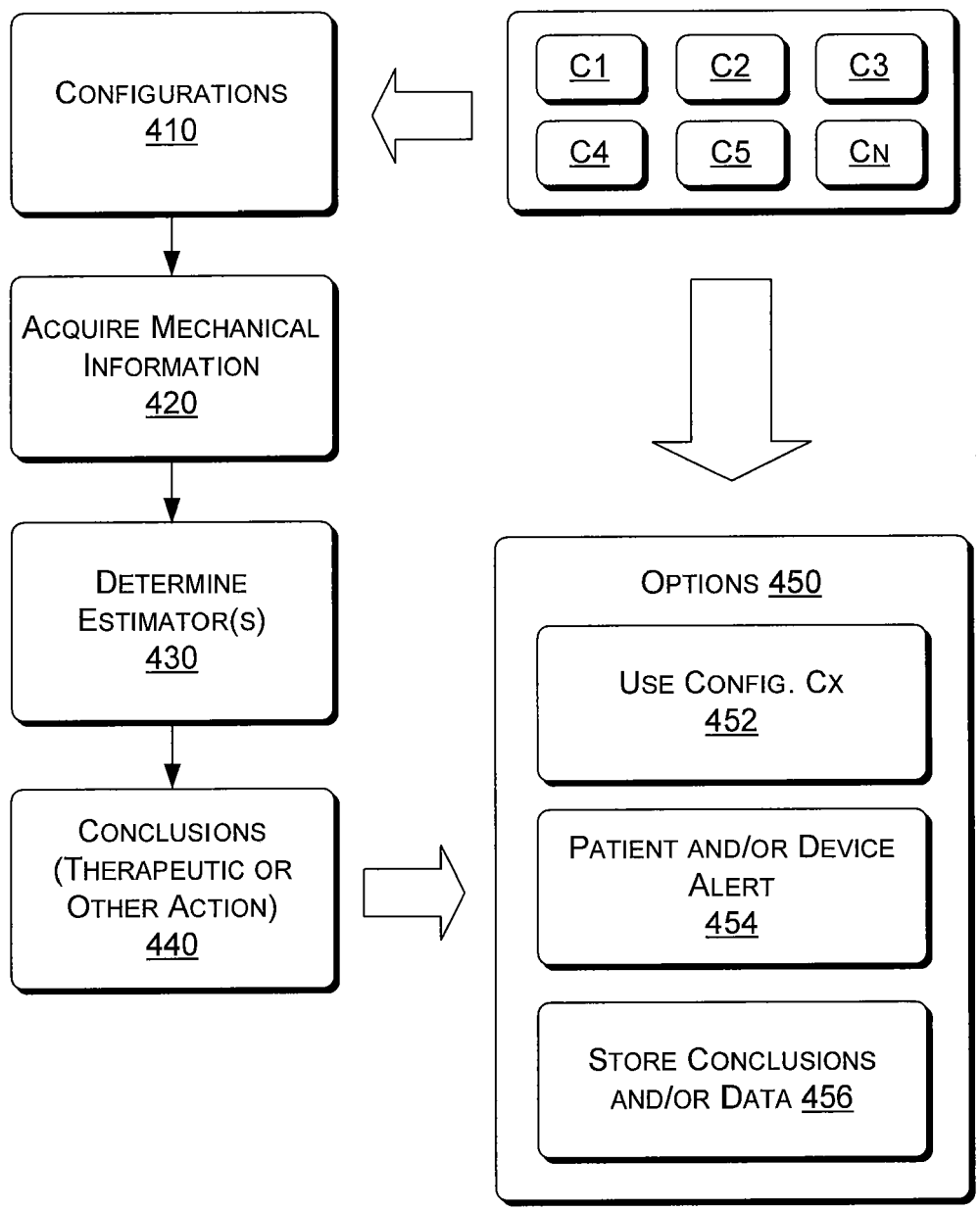
FIG. 4 is a block diagram of the exemplary method of FIG. 3 along with various options.

FIG. 4 shows the exemplary method 400 with various configurations 410 (C1, C2, . . . , Cn) and options 450. As mentioned, a configuration may be defined based on factors such as electrode position (e.g., with respect to some physiological feature of the heart or another electrode), stimulation parameters for an electrode or electrodes and, where appropriate, one or more interelectrode timings. Hence, with reference to FIG. 1, C1 may be a configuration that relies on the RV tip electrode 128, the RV ring electrode 130, the LV tip electrode 122 and the LV ring electrode 124 while C2 may be a configuration that relies on the same electrodes as C1 but where the stimulation polarity for the LV electrodes is reversed. Further, C3 may rely on the same electrodes where the timing between delivery of a stimulus to the RV and delivery of a stimulus to the LV is different compared to C1. Yet further, C4 may rely on the same electrodes where the duration of a stimulus to the RV is different compared to C1. In these foregoing examples, configurations provide for one or more electrodes to deliver energy to stimulate the right ventricle and for one or more electrodes to deliver energy to stimulate the left ventricle. In other examples, configurations may provide for stimulation of a single chamber at one or more sites, stimulation of one chamber at a single site and another chamber at multiple sites, multiple chambers at multiple sites per chamber, etc.

In the acquisition block 420, acquisition occurs for mechanical information where such information pertains to one or more configurations. In the VE determination block 430, one or more VEs are determined based at least in part on the mechanical information. The conclusions block 430 provides for therapeutic or other action, which may be selected from one or more options 450.

In the example of FIG. 4, the one or more options 450 include selection of a configuration 452 (e.g., Cx, where x is a number selected from 1 to n), issuance of a patient and/or device alert 454 that pertains to condition of a patient or a condition of a device or associated lead(s) or electrode(s), and storage of conclusion(s) and/or data 456. The options 450 may be associated with the configurations 410, as indicated by an arrow. For example, storage of conclusions and/or data 456 may also store specific configurations, a generalization of the configurations (e.g., one or more shared characteristics), a device/system arrangement (e.g., where the number and types of configurations would be known based on the arrangement), etc.

As described herein, an exemplary method can include: positioning one or more electrodes within the heart and/or surrounding space (e.g., intra-chamber, intra-vascular, intra-pericardial, etc., which may be collectively referred to as "cardiac space"); and acquiring mechanical information (e.g., via one or more measured potentials) to determine a location, locations or displacement for at least one of the one or more electrodes using an electroanatomic mapping system (e.g., the ENSITE® NavX system or other system with appropriate features). In such a method, the positioned electrodes may be configured for acquisition of electrical information (e.g., IEGMs). Further, with respect to acquisition of information, an acquisition system may operate at an appropriate sampling rate. For example, an acquisition system for mechanical information may operate at a sampling rate of about 100 Hz (e.g., the ENSITE® NavX system can sample at about 93 Hz) and an acquisition system for electrical information may operate at a sampling rate of about 1200 Hz (e.g., in unipolar, bipolar or other polar arrangement).

As explained, the mechanical information is used to determine one or more estimators. In turn, a therapy may be selected or optimized or condition diagnosed based at least in part on the one or more estimators.

An exemplary method may include preparing a patient for both implant of a device such as the device 100 of FIGS. 1 and 2 and for electroanatomic mapping study. Such preparation may occur in a relatively standard manner for implant prep, and using the ENSITE® NavX system or other similar technology for the mapping prep. As described herein, any of a variety of electroanatomic mapping or locating systems that can locate indwelling electrodes in and around the heart may be used.

Once prepped, a clinician or robot may place leads and/or catheters in the patient's body, including any leads to be chronically implanted as part of a CRT system, as well as optional additional electrodes that may yield additional information (e.g., to increase accuracy by providing global information or other information).

After an initial placement of an electrode-bearing catheter or an electrode-bearing lead, a clinician may then connect one or more electrodes to an electroanatomic mapping or locating system. The term "connection" can refer to physical electrical connection or wireless connection (e.g., telemetric, RF, ultrasound, etc.) with the electrodes or wireless connection with another device that is in electrical contact with the electrodes.

Once an appropriate connection or connections have been made, real-time position data for one or more electrodes may be acquired for various configurations or conditions. For example, position data may be acquired during normal sinus rhythm; pacing in one or more chambers; advancing, withdrawing, or moving a location of an electrode; pacing one or more different electrode configurations (e.g. multisite pacing); or varying inter-stimulus timing (e.g. AV delay, VV delay).

In various examples, simultaneous to the position recording, an intracardiac electrogram from each electrode can also be recorded and associated with the anatomic position of the electrode. While various examples refer to simultaneous acquisition, acquisition of electrical information and acquisition of mechanical information may occur sequentially (e.g., alternate cardiac cycles) or interleaved (e.g., both acquired during the same cardiac cycle but offset by sampling time or sampling frequency).

In various exemplary methods, electrodes within the cardiac space may be optionally positioned at various locations (e.g., by continuous movement or by discrete, sequential moves), with a mapping system recording the real-time motion information at each electrode position in a point-by-point manner. Such motion data can by associated with a respective anatomic point from which it was collected. By moving the electrodes from point to point during an intervention, the motion data from each location can be incorporated into a single map, model, or parameter. As described in more detail below, mechanical information (e.g., motion information) can be used to estimate a local volume as a local estimator (e.g., a local volume estimator, LVE), a regional volume as a regional estimator (e.g., a regional volume estimator, RVE) and/or a global volume as a global estimator (e.g., a global volume estimator, GVE).

As explained, an exemplary method may include determining one or more of estimators. In turn, an algorithm or a clinician may select a configuration (e.g., electrode location, multisite arrangement, AV/VV timing) that yielded the best value for an electromechanical delay parameter and use the selected configuration as a chronic configuration for the CRT system. Such a chronic configuration may be optionally updated from time to time (e.g., during a follow-up visit, in a patient environment, etc., depending on specific capabilities of a system).

Various exemplary methods, using either a single parameter or a combination of more than one parameter, may automatically select a configuration, present an optimal configuration for acknowledgement by a clinician, or present various configurations to a clinician along with pros and cons of each configuration (e.g., in objective or subjective terms). For example, a particular configuration may be associated with a high power usage that may excessively drain a power source of an implantable device (e.g., device battery 276). Other pros and cons may pertain to patient comfort (e.g., pain, lack of pain, overall feeling, etc.).

An exemplary method may rely on certain equipment at time of implant or exploration and other equipment after implantation of a device to deliver a cardiac therapy. For example, during an intraoperative procedure, wireless communication may not be required; whereas, during a follow-up visit, measured potentials for position of chronically implanted electrodes (e.g., mechanical information) and of measured IEGMs using chronically implanted electrodes (e.g., electrical information) may be communicated wirelessly from an implanted device to an external device. With respect to optimization of a chronically implanted system, in general, electrode location will not be altered, but other parameters altered to result in an optimal configuration (e.g., single- or multi-site arrangement, polarity, stimulation energy, timing parameters, etc.).

As discussed herein, various exemplary techniques deliver current and measure potential where potential varies typically with respect to cardiac mechanics (e.g., due to motion). For example, electrodes for delivery of current may be placed at locations that do not vary significantly with respect to cardiac mechanics while one or more electrodes for measuring potential may be placed at a location or locations that vary with respect to cardiac mechanics. Alternatively, electrodes for measuring potential may be placed at locations that do not vary significantly with respect to cardiac mechanics while one or more electrodes for delivery of current may be placed at a location or locations that vary with respect to cardiac mechanics. Various combinations of the foregoing arrangements are possible as well. Electrodes may be associated with a catheter or a lead. In some instances, an electrode may be a "stand-alone" electrode, such as a case electrode of an implantable device (see, e.g., the case electrode 200 of the device 100 of FIGS. 1 and 2).

Figure 5:
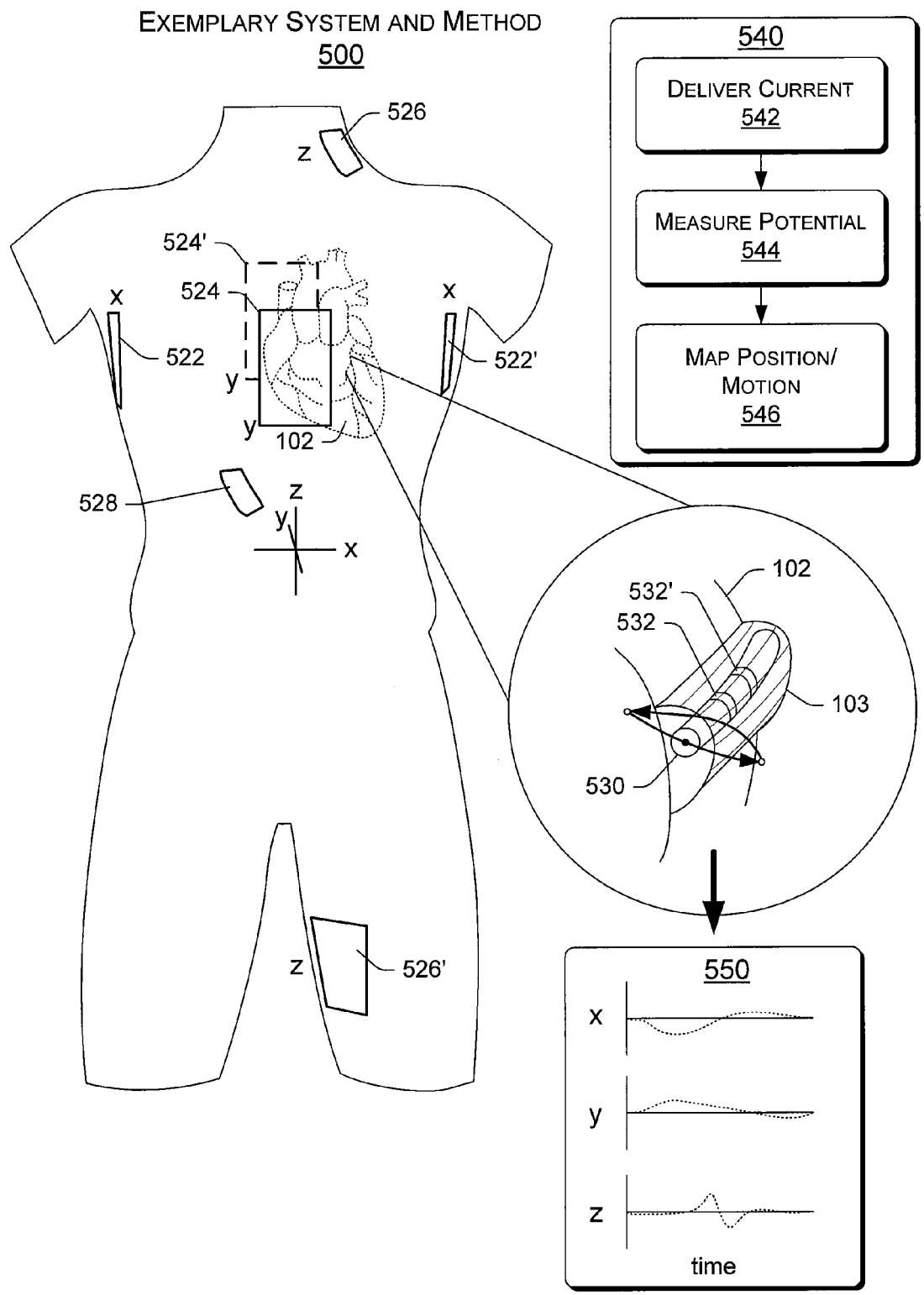
FIG. 5 is an exemplary arrangement of a lead and electrodes for acquiring mechanical information and optionally other information.

FIG. 5 shows an arrangement and method 500 that may rely in part on a commercially available system marketed as ENSITE® NavX navigation and visualization system (see also LocaLisa system). The ENSITE® NavX system is a computerized storage and display system for use in electrophysiology studies of the human heart. The system consists of a console workstation, patient interface unit, and an electrophysiology mapping catheter and/or surface electrode kit. By visualizing the global activation pattern seen on color-coded isopotential maps in the system, in conjunction with the reconstructed electrograms, an electrophysiologist can identify the source of an arrhythmia and can navigate to a defined area for therapy. The ENSITE® system is also useful in treating patients with simpler arrhythmias by providing non-fluoroscopic navigation and visualization of conventional electrophysiology (EP) catheters.

As shown in FIG. 5, electrodes 532, 532', which may be part of a standard EP catheter 530 (or lead), sense electrical potential associated with current signals transmitted between three pairs of surface electrode patches 522, 522' (x-axis), 524, 524' (y-axis) and 526, 526' (z-axis). An addition electrode patch 528 is available for reference, grounding or other function. The ENSITE® NavX System can also collect electrical data from a catheter and can plot a cardiac electrogram 570 from a particular location (e.g., cardiac vein 103 of heart 102). Information acquired may be displayed as a 3-D isopotential map and as virtual electrograms. Repositioning of the catheter allows for plotting of cardiac electrograms from other locations. Multiple catheters may be used as well. A cardiac electrogram or electrocardiogram (ECG) of normal heart activity (e.g., polarization, depolarization, etc.) typically shows atrial depolarization as a "P wave", ventricular depolarization as an "R wave", or QRS complex, and repolarization as a "T wave". The ENSITE® NavX system may use electrical information to track or navigate movement and construct three-dimensional (3-D) models of a chamber of the heart.

A clinician can use the ENSITE® NavX system to create a 3-D model of a chamber in the heart for purposes of treating arrhythmia (e.g., treatment via tissue ablation). To create the 3-D model, the clinician applies surface patches to the body. The ENSITE® NavX system transmits an electrical signal between the patches and the system then senses the electrical signal using one or more catheters positioned in the body. The clinician may sweep a catheter with electrodes across a chamber of the heart to outline structure. Signals acquired during the sweep, associated with various positions, can then be used to generate a 3-D model. A display can display a diagram of heart morphology, which, in turn, may help guide an ablation catheter to a point for tissue ablation.

With respect to the foregoing discussion of current delivery and potential measurement, per a method 540, a system (e.g., such as the ENSITE® NavX system) delivers low level separable currents from the three substantially orthogonal electrode pairs (522, 522', 524, 524', 526, 526') positioned on the body surface (delivery block 542). The specific position of a catheter (or lead) electrode within a chamber of the heart can then be established based on three resulting potentials measured between the recording electrode with respect to a reference electrode, as seen over the distance from each patch set to the recording tip electrode (measurement block 544). Sequential positioning of a catheter (or lead) at multiple sites along the endocardial surface of a specific chamber can establish that chamber's geometry, i.e., position mapping (position/motion mapping block 546). Where the catheter (or lead) 530 moves, the method 540 may also measure motion.

In addition to mapping at specific points, the ENSITE® NavX system provides for interpolation (mapping a smooth surface) onto which activation voltages and times can be registered. Around 50 points are required to establish a surface geometry and activation of a chamber at an appropriate resolution. The ENSITE® NavX system also permits the simultaneous display of multiple catheter electrode sites, and also reflects real-time motion of both ablation catheters and those positioned elsewhere in the heart.

The ENSITE® NavX system relies on catheters for temporary placement in the body. Various exemplary techniques described herein optionally use one or more electrodes for chronic implantation. Such electrodes may be associated with a lead, an implantable device, or other chronically implantable component. Referring again to FIG. 3, the configuration block 310 indicates that intraoperative configurations 312 and chronic configurations 314 may be available. Intraoperative configurations 312 may rely on a catheter and/or a lead suitable for chronic implantation.

With respect to motion, the exemplary system and method 500 may track motion of an electrode in one or more dimensions. For example, a plot 550 of motion versus time for three dimensions corresponds to motion of one or more electrodes of the catheter (or lead) 530 positioned in a vessel 103 of the heart 102 where the catheter (or lead) 530 includes the one or more electrodes 532, 532'. Two arrows indicate possible motion of the catheter (or lead) 530 where hysteresis may occur over a cardiac cycle. For example, a systolic path may differ from a diastolic path. An exemplary method may analyze hysteresis for any of a variety of purposes including selection of a stimulation site, selection of a sensing site, diagnosis of cardiac condition, etc.

The exemplary method 540, as mentioned, includes the delivery block 542 for delivery of current, the measurement block 544 to measure potential in a field defined by the delivered current and the mapping block 546 to map motion based at least in part on the measured potential. According to such a method, motion during systole and/or diastole may be associated with electrical information. Alone, or in combination with electrical information, the mechanical motion information may be used for selection of optimal stimulation site(s), determination of hemodynamic surrogates (e.g., surrogates to stroke volume, contractility, etc.), optimization of CRT, placement of leads, determination of pacing parameters (AV delay, VV delay, etc.), etc.

The system 500 may use one or more features of the aforementioned ENSITE® NavX system. For example, one or more pairs of electrodes (522, 522', 524, 524', 526, 526') may be used to define one or more dimensions by delivering an electrical signal or signals to a body and/or by sensing an electrical signal or signals. Such electrodes (e.g., patch electrodes) may be used in conjunction with one or more electrodes positioned in the body (e.g., the electrodes 532, 532').

The exemplary system 500 may be used to track motion of one or more electrodes due to systolic motion, diastolic motion, respiratory motion, etc. Electrodes may be positioned along the endocardium and/or epicardium during a scouting or mapping process for use in conjunction with electrical information. Such information may also be used alone, or in conjunction with electrical information, for identifying the optimal location of an electrode or electrodes for use in delivering CRT. For example, a location may be selected for optimal stimulation, for optimal sensing, or other purposes (e.g., anchoring ability, etc.).

With respect to stimulation, stimulation may be delivered to control cardiac mechanics (e.g., contraction of a chamber of the heart) and motion information may be acquired where the motion information is associated with the controlled cardiac mechanics. An exemplary selection process may identify the best stimulation site based on factors such as electrical activity, electromechanical delay, extent of motion, synchronicity of motion where motion may be classified as systolic motion or diastolic motion. In general, motion information corresponds to motion of an electrode or electrodes (e.g., endocardial electrodes, epicardial electrodes, etc.) and may be related to motion of the heart.

Figure 6:
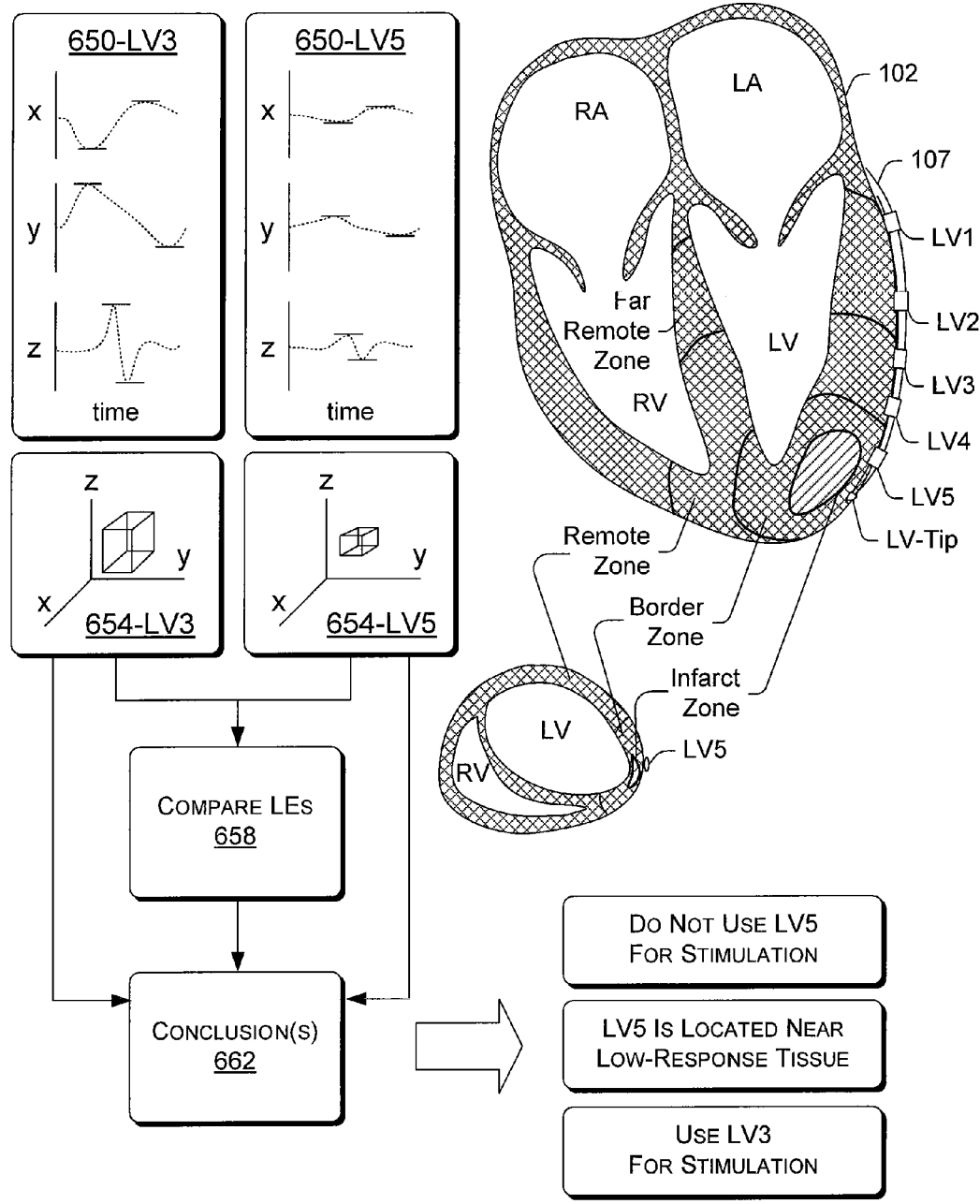
FIG. 6 is a simplified diagram illustrating an exemplary method for local volume estimation with reference to an approximate anatomical diagram of the heart and various electrodes.

FIG. 6 shows an exemplary method 600 for local volume estimation with reference to an approximate anatomical diagram of the heart 102 and a series of electrodes of a left ventricular lead 107. The series of electrodes LV1-LV5 and LV-Tip may be positioned in a vein that extends across a wall of the left ventricle (see, e.g., the lead 106 of FIG. 1). In the example of FIG. 6, the cross-sectional view of the heart 102 shows an infarct region or zone, a neighboring border zone, a remote zone and a far remote zone.

With respect to classification of damaged myocardial regions, the International Classification of Diseases, Clinical Modification (ICD-9-CM) has been used to code and classify morbidity data from the inpatient and outpatient records, physician offices, and most National Center for Health Statistics (NCHS) surveys. As described herein, a region, zone or border identified may be optionally classified using one or more of the ICD-9-CM diagnosis codes. For example, ICD-9-CM diagnosis codes include 410.01 (anterolateral wall, acute myocardial infarction-initial episode), 410.11 (other anterior wall, acute myocardial infarction-initial episode), 410.21 (inferolateral wall, acute myocardial infarction-initial episode), 410.31 (inferoposterior wall, acute myocardial infarction-initial episode), 410.41 (other inferior wall, acute myocardial infarction-initial episode), 410.51 (other lateral wall, acute myocardial infarction-initial episode), 410.61 (true posterior wall, acute myocardial infarction-initial episode), 410.71 (subendocardial, acute myocardial infarction-initial episode), 410.81 (other specified sites, acute myocardial infarction-initial episode) and 410.91 (unspecified site, acute myocardial infarction-initial episode). Codes may be of a more general nature while information acquired using an exemplary method may be more specific, for example, as indicated by the cross-sectional view of FIG. 6.

The exemplary method 600 includes acquiring mechanical information for at least one electrode, as illustrated by a plot 650-LV3 for the electrode LV3 and a plot 650-LV5 for the electrode LV5. In this example, the mechanical information is acquired with reference to a three-dimensional coordinate system (e.g., Cartesian coordinate system with coordinates x, y, z). The plots 650-LV3 and 650-LV5 also indicate maxima and minima for each of the three coordinates. Based on such mechanical information, the method 600 can determine a local estimator for the electrode LV3 and a local estimator for the electrode LV5, as indicated by a volume in a plot 654-LV3 and a volume in a plot 654-LV5 where each volume may be constructed based on the maxima and minima of the plots 650-LV3 and 650-LV5, respectively.

The method 600 optionally includes a comparison block 658 to compare the local estimators. For example, the LE for the electrode LV5 is much smaller than the LE for the electrode LV3. As indicated, the electrode LV5 is closer to the infarct zone that the electrode LV3. Thus, based on a comparison, a conclusion block 662 may conclude that less motion from the electrode LV5 corresponds to diminished tissue viability. However, other factors may be accounted for in making a conclusion. For example, the electrode LV5 is also closer to the apex of the heart 102. Various studies have shown that the apex of the heart may remain somewhat "stationary" during contraction as the base tends to coil downward during contraction (e.g., electrode LV1 may be expected to have the greatest displacement along the long axis of the left ventricle). Such a conclusion may be tested by delivering a stimulation pulse using the electrode LV5 and delivering a stimulation using the electrode LV3. If the tissue near the electrode LV5 is damaged, then stimulation at the LV5 electrode site may require a greater stimulation energy, exhibit a greater delay between delivery and mechanical activation, etc. Hence, various exemplary methods may include verification techniques to help verify or make a conclusion.

In the example of FIG. 6, the conclusions block 662 may conclude, based at least in part on one or more of the LEs, that the electrode LV5 should not be used for stimulation, that the electrode LV5 is located near low-responsive tissue, that the electrode LV3 should be used for stimulation, etc. As indicated, the conclusions block 662 may make a conclusion based in part on a single LE (see, e.g., arrows from the plots 654-LV3 and 654-LV5 to the conclusions block 662).

As explained with respect to FIG. 6, a local estimator does not attempt to estimate a physiologic cardiac volume, but rather to characterize how a local piece of myocardium moves based on electrode motion. In various scenarios, an increase in a local estimator (e.g., larger local swept path of an electrode) can indicate better local myocardial performance. Where local estimators are determined for multiple locales (e.g., with some intervening distance), global performance may be inferred or an index for global performance determined.

As shown in the plots 654-LV3 and 654-LV5, a local estimator can be determined based on linear dimensions or volume of a "bounding box" defined by an electrode's trajectory, for example, over a cardiac cycle. Such local estimators may rely on the same coordinate system of an electroanatomic locating system such as the ENSITE® NavX system.

Defining properties of a bounding box can include edges aligned with the coordinate system axes with edge lengths given by the peak-to-peak motion of the electrode along each coordinate axis (e.g., minimum and maximum location for each coordinate dimension). From these properties, each electrode can be "enclosed" in such a box for each beat. While the example of FIG. 6 shows local estimators in a Cartesian coordinate system, other coordinate systems (e.g., conventional or custom) may be used. For example, a coordinate system with dimensions aligned with the heart's long and short axes may be used.

While the example of FIG. 6 shows volumes as cubes (i.e., boxes), the shape that bounds a trajectory can be selected from any of a variety of shapes, which may depend on the coordinate system selected. For example, a local estimator may be a primitive, such as a sphere, pyramid, prism, cylinder, section of a cone, section of a cylindrical wall, etc. The local estimator may be computed based on the bounding values of motion (e.g., maximum and minimum in a particular coordinate system) or alternatively based on optimization such as least-squares that computes the best-fit surface for the motion throughout a cardiac cycle. Hence, a min/max approach requires two points whereas more points could be used for a trace. Where more points are used, an exemplary method may include fitting to predefined shapes, splines or shape models. For example, a model may allow for fitting to a cylinder or other shape (e.g., 2D or 3D) such that motion can be tracked and possibly analyzed using the fitted model. Local motion of an electrode may be an oval, ellipse, or more complex. For example, various trials show that motion of an electrode in the coronary sinus can be in 3D and fitted to a model of a 3D shape such as a cylinder.

As discussed herein, a "local estimator" (LE) may be a line, a curve, an area or a volume. For example, in a two point min/max approach, a line may provide an LE whereas if three points are used, then a line, a curve or an area may provide an LE. Where a volumetric model is used, in general, at least two points and preferably three or more points are used to provide an LE. In absence of a specific volumetric model, at least four points are required to provide an LE (e.g., consider a tetrahedron).

With respect to cylinders as a local estimators, a bounding cylinder may have a longitudinal axis aligned with the long axis of the heart or left ventricle (e.g., from base to apex). The long axis may be estimated based on the relative positions of electrodes in proximity to known anatomic landmarks, such as the direction pointing from the RV apex to the ostium of the coronary sinus or to a right atrial lead, or may be estimated based on a prescribed orientation with respect to the body surface patches, or may be estimated by comparison or registration with a real-time or previously acquired image such as rotational fluoroscopy, CT scan, echo, or MRI.

An analysis of a bounding shape may provide insight into cardiac performance. As mentioned, volume of a bounding shape can be used as an estimate of trajectory size for an electrode, which can be implemented in an algorithm with few calculations. For example, an exemplary algorithm may acquire position data for an electrode, determine a maximum value along a coordinate system dimension, determine a minimum value along the coordinate system dimension, subtract the values to determine a displacement along the coordinate system dimension, repeat for two other coordinate systems dimensions and then multiple the displacement values for the three coordinate system dimensions to provide a local estimator.

Trajectory information (e.g., length, width, and height, or radius and height, of a bounding shape), can yield orientation of myocardial motion, particularly in where the bounding volume is aligned with a physiologically relevant coordinate system. For example, where the shape of a local estimator is a cylinder, radii of respective bounding cylinders can be indicative of short-axis contraction while heights of respective bounding cylinders can be indicative of long-axis contraction. Based on such information, an intervention may be chosen that improves both short- and long-axis contraction. Such an intervention may be more beneficial to the patient than one that improves only one aspect of contraction. As such, the aspect ratio of a bounding volume can be used to determine the relative contributions of various components of contraction.

Another approach can select two points along an electrode trajectory and then establish a line or a vector between the two points. Such an approach can also reduce computation overhead, which may allow for presentation of behavior in near real-time. For example, an exemplary approach can rely on length and orientation of a line connecting a minimum point and a maximum point along a dimension, or connecting an end diastolic (ED) point and an end systolic (ES) point.

As described herein, local estimators for two or more electrodes may be summed and the sum used as an indicator of cardiac performance. Trial estimates on a canine model indicate that a sum or average of the local volumes of bounding boxes on electrodes of a CRT system reasonably reflects cardiac performance as measured by invasive LV pressure. Trials demonstrated that the volumes of individual electrode bounding boxes increased in CRT and LV pacing modes versus sinus rhythm and RV pacing modes in a canine model of heart failure (HF) and left bundle branch block (LBBB).

Figure 7:
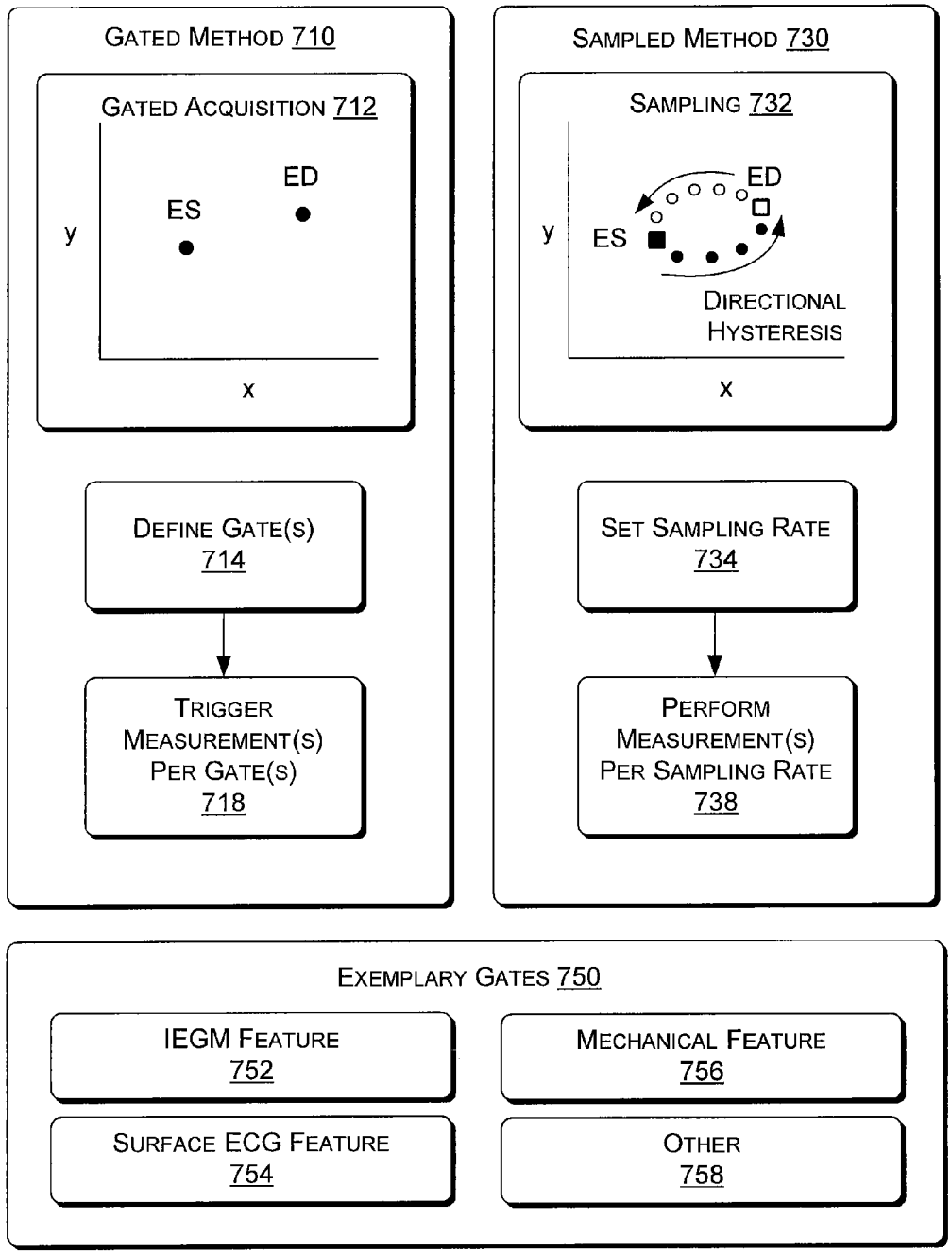
FIG. 7 is a block diagram of two exemplary acquisition methods for acquiring mechanical information for one or more electrodes.

As mentioned, an exemplary method may rely on one or more positions along an electrode trajectory where the one or more positions correspond to a point in time of the cardiac cycle. FIG. 7 shows an exemplary gated acquisition method 710 and an exemplary sampled acquisition method 730. A gated acquisition plot 712 and a sampling plot 732 are shown in two dimensions (x and y) to facilitate explanation, noting that position data may be acquired for a single dimension or more than two dimensions.

In the gated method 710, one or more gates are defined in a definition block 714 and then in a trigger block 718, the one or more gates are used to trigger one or more measurements (e.g., position). A block 750 includes some exemplary gates. Specifically, the block 750 includes an IEGM feature gate 752, a surface ECG feature gate 754, a mechanical feature gate 756 and one or more other gates 758. The IEGM feature gate 752 or the surface ECG feature gate 754 may be a QRS complex, an R-wave, a T-wave, a P-wave, a feature of an evoked response (e.g., atrial or ventricular), etc. The mechanical feature gate 756 may be a derivative gate, an amplitude gate, etc. For example, a derivative gate may monitor slope or acceleration of an electrode's position and then acquire a value where a derivative changes sign or where acceleration reaches a maximum or minimum. An amplitude gate may monitor amplitude of an electrode's position in one or more dimensions and then acquire a value where the position reaches, exceeds or falls below an amplitude threshold or limit. Other gates 758 may include pressure gates, respiration gates, pacing gates, etc. For example, where pacing occurs, a gate may trigger a measurement of an electrode's position based on the delivery of time of a pacing pulse and optionally a delay (e.g., pacing time plus 40 ms). With respect to pressure, a ventricular pressure or an aortic pressure may be used. In various examples, a gate allows for acquiring position information with respect to some other event in a fairly reliable manner.

In the sampling method 730, the plot 732 includes filled and open circles that represent paths of an electrode along the x and y dimensions between end diastole (ED, open square) and end systole (ES, filled square). As indicated, hysteresis exists as the path of the electrode from end systole (ES) to end diastole (ES) differs from the path of the electrode from end diastole (ED) to end systole (ES). The method 730 includes a set block 734 that sets a sampling rate for measuring position information and a measurement block 738 for measuring positions according to the sampling rate.

In the method 710 and 730, where multiple electrodes are tracked, a position measurement for each of the electrodes may be offset slightly in time, acquired using a multiplexer, acquired in parallel, etc.

As described herein it is particularly useful in the computation of some estimators to gate acquisition of a position, or otherwise to mark, a position as corresponding to an end diastolic (ED) point in time and a position as corresponding to an end systolic (ES) point in time. Where ED and ES appear in the figures or description, it is assumed that gating or other techniques allowed for such identification. The terms "end diastolic point" and "end systolic point" may be used to refer to positions of electrodes at the end-diastolic gated and end-systolic gated time points, respectively.

In practice, any point in a cardiac cycle may be used to gate position data. A gate point may be referred to as, $p_i$, where "i" is a number or letter that identifies a specific point in a cardiac cycle. The point in the cardiac cycle may be identified by a particular electrical or motion-based characteristic, for example the point of a zero-crossing of the signal, or it may refer to a particular phase of the cardiac cycle such as a fraction of the R-R interval for example.

As mentioned, it is possible to gate data collection to portions of a trajectory (see, e.g., mechanical feature 756 of FIG. 7). For example a maximum or a minimum displacement from a reference point, or extreme positions along a trajectory for a cardiac cycle may be taken as gates. The terms "max point" and "min point" may refer to the position that represents the maximum or minimum distance from a given reference point, respectively, and may also refer to the position at which a value of a particular parameter is maximized or minimized. Additional estimators may rely on trajectory of electrode positions throughout an entire cardiac cycle. Such estimators increase in fidelity with an increase in sample frequency of the position signal (e.g., consider the sampling plot 732 of FIG. 7).

The respective trajectories of electrodes or the respective end diastolic (ED) and end systolic (ES) points of electrodes can be used to compute any one or more of the estimation parameters described herein. An exemplary method can compute a parameter for a given configuration or configurations, including but not limited to location of pacing electrode, choice of one or more pacing electrodes, pacing mode, pacing sequence, and timing of pacing stimuli. Where configurations correspond to CRT, a configuration yielding the best score for a single estimation parameter or a composite of several parameters can be selected as the configuration of optimal CRT. For example, a volume estimator may globally approximate ejection fraction (EF); maximizing a patient's EF is one way to provide benefit from CRT.

Figure 8:
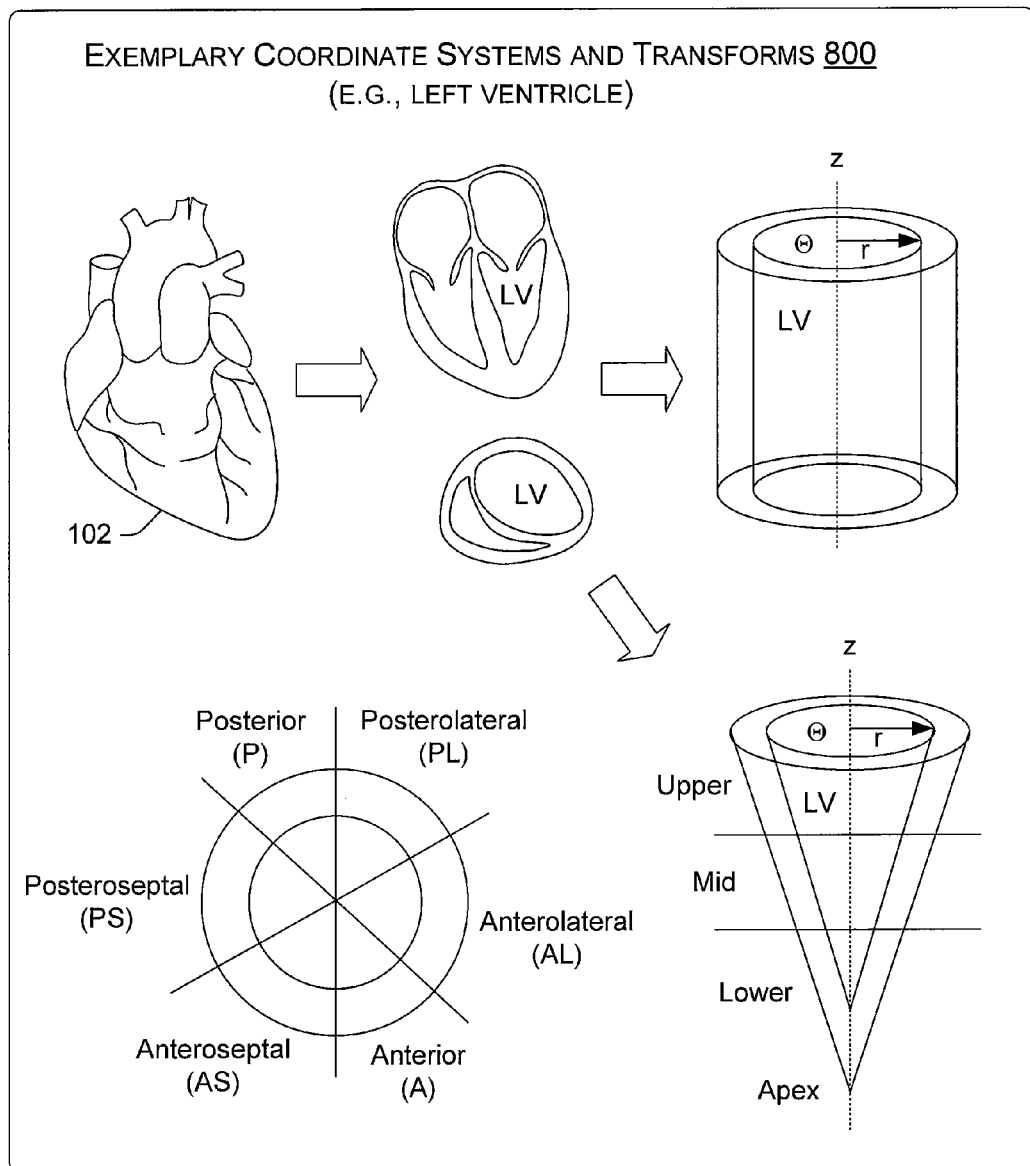
FIG. 8 is a series of diagrams that illustrate various coordinate systems and transforms or mappings for modeling a ventricle of the heart.

FIG. 8 shows some exemplary coordinate systems and transforms 800 that aim to facilitate description of examples for regional estimators (REs) and global estimators (GEs). FIG. 8 shows a heart 102 and two cross-sections of the heart 102. In the cross-sections, the left ventricle (LV) is labeled. As seen, the left ventricle has a somewhat cylindrical shape that can be more accurately represented as a cone. When the left ventricle is modeled as a cylinder or as a cone, a cylindrical coordinate system may be used with dimensions r, z and θ. The heart 102 can be further defined by sections along a main axis (z) from apex, lower, mid and upper (e.g., corresponding to the base of the left ventricle). In the azimuthal dimension, the heart 102 may be defined by anterior (A), anterolateral (AL), posterolateral (PL), posterior (P), posteroseptal (PS) and anteroseptal (AS) sections; noting that other definitions were presented above with respect to cardiac damage.

FIGS. 9, 10, 11, 12, 13 and 14, which describe electrode position mapping (FIG. 9), regional estimators (FIG. 10), regional estimators and dysynchrony (FIG. 11), plots of local estimators and regional estimators (FIG. 12), global estimators (FIG. 13) and trajectory techniques (FIG. 14) refer or may refer to a cylindrical model of the left ventricle; noting that other types of models or coordinate systems may be used.

Figure 9:
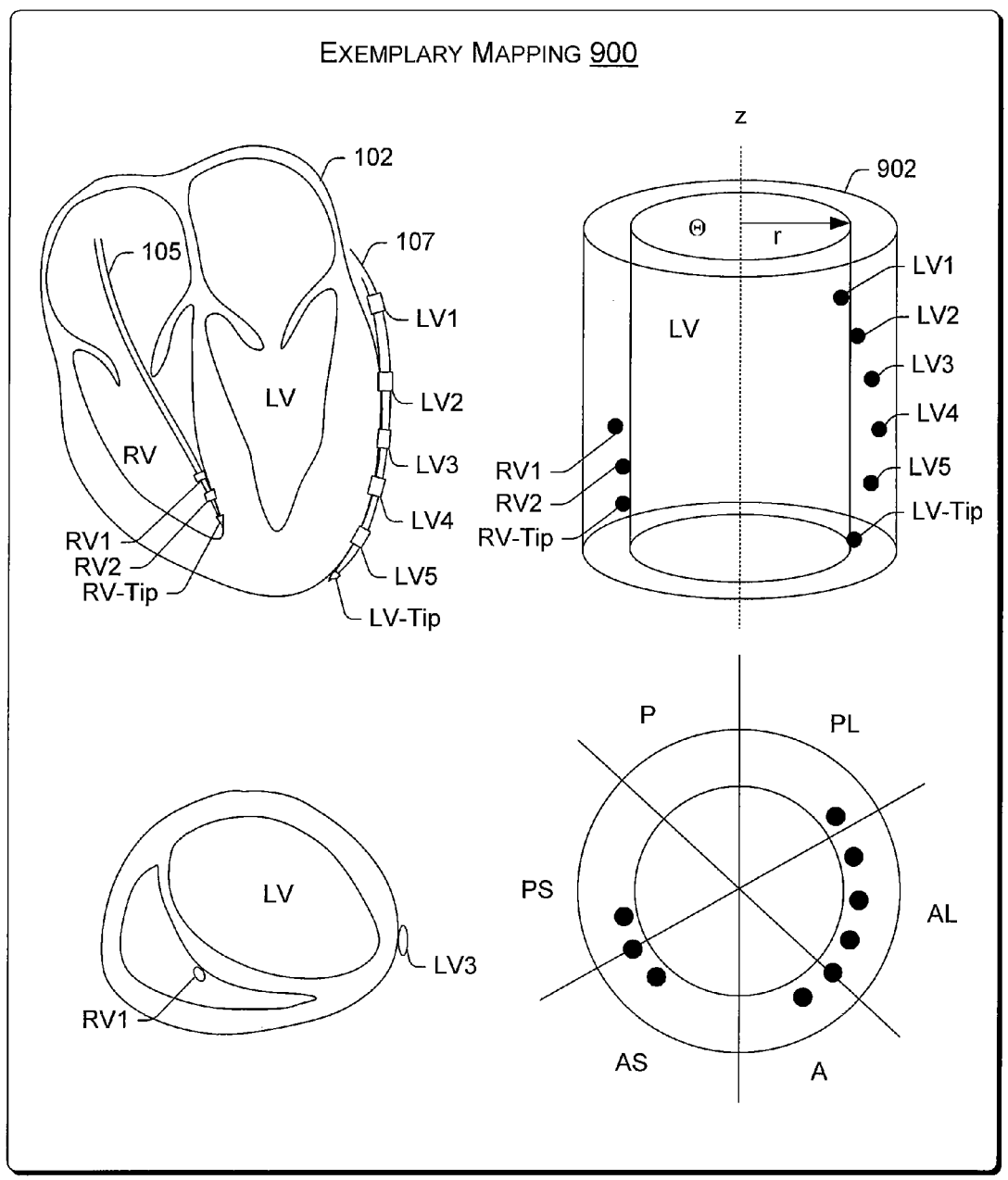
FIG. 9 is an approximate anatomical diagram of the heart including various electrodes and a transformed representation of the left ventricle of the heart that illustrates various electrode locations.

FIG. 9 shows a cross-section of the heart 102 substantially along the long or major axis of the left ventricle (r,z-plane) and a cross-section of the heart 102 taken substantially along the minor axis of the left ventricle (r,θ-plane). As shown, a right ventricular lead 105 is positioned in the right ventricle with electrodes RV1, RV2 and RV-Tip positioned at or near the septal wall. A left ventricular lead 107 is positioned along a wall of the left ventricle with electrodes LV1-LV5 and LV-Tip. The positions of these electrodes are shown with respect to a perspective view and a cross-sectional view of a cylinder model 902 of the left ventricle. The definition system of FIG. 8 indicates that the electrodes are positioned in five of the six radial sections (i.e., pie-like slices of the cylindrical wall). Given such an arrangement, position data may be acquired with respect to various points in time to thereby understand better cardiac performance, particularly performance of the left ventricle.

Figure 10:
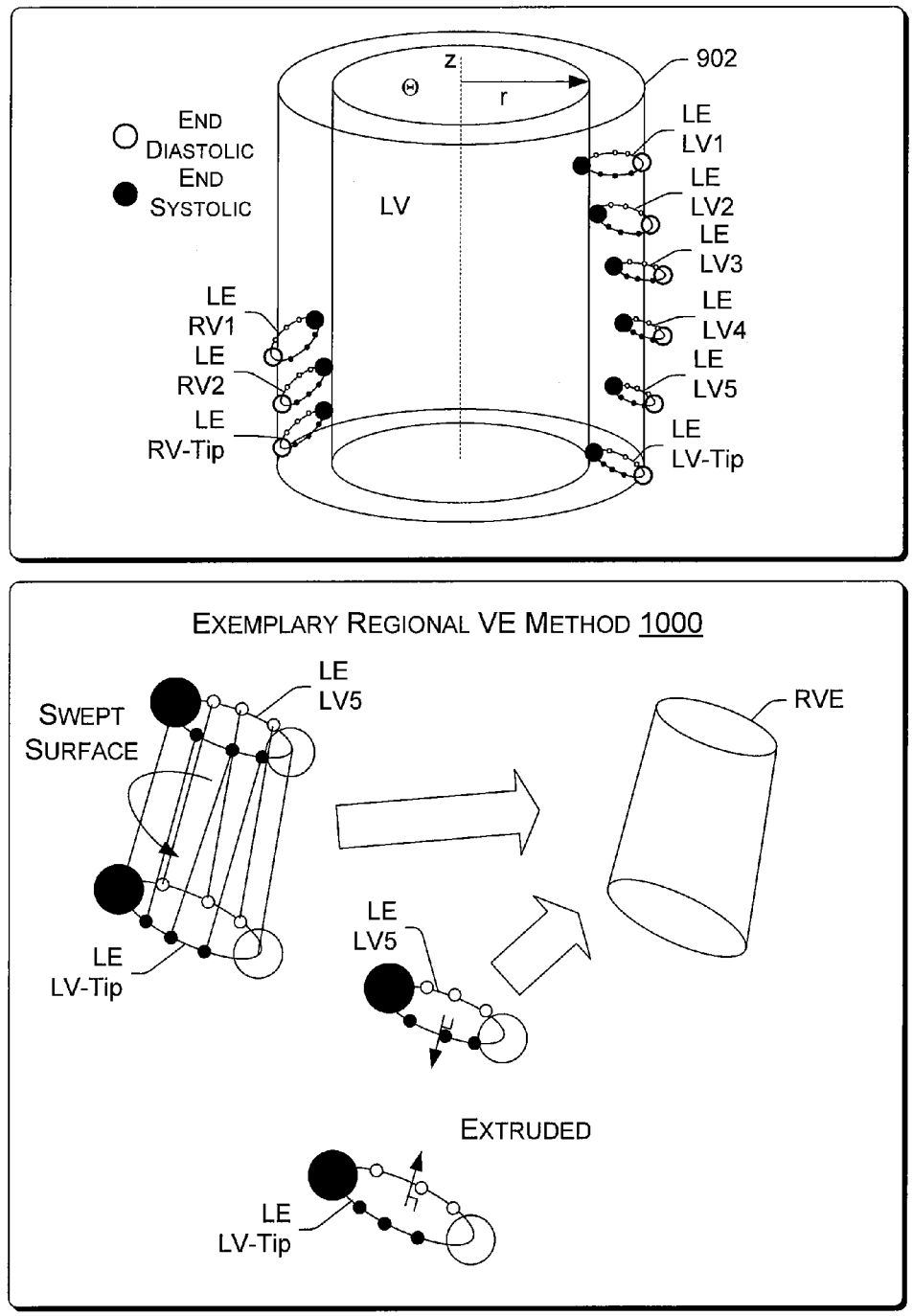
FIG. 10 is a representation of the left ventricle of the heart along with an illustration of an exemplary method to determine a regional volume estimator based on mechanical information for two or more electrodes.

FIG. 10 shows the cylinder model 902 of the left ventricle along with local estimators for each of the 9 electrodes. In the example of FIG. 10, each of the local estimators (LE) includes a marker for end diastolic (ED, large open sphere) and a marker for end systolic (ES, large filled sphere). Additional points are shown with smaller markers (open markers progressing toward ES and closed markers progressing toward ED).

As described herein, given two local estimators for two different electrodes (e.g., based on mechanical information), a regional estimator may be determined, as shown in a method 1000. The method 1000 determines a regional estimator (RE) for a region that includes the LV-Tip electrode and the LV5 electrode. In this example, the RE is determined by either sweeping a surface around the perimeter of the LE for LV5 and the LE for LV-Tip or by extruding the LEs, for example, according to normal directions or other vector or vectors. In either instance, a RE results that represents the motion space for the adjacent LV5 and LV-Tip electrodes.

According to the example of FIG. 10, an exemplary method can rely on an extrusion technique to extrude a surface in one or more directions to create a regional estimator. For example, an area swept by a single electrode trajectory over the course of a cardiac cycle can be extruded toward another electrode that sweeps its own respective area. Another exemplary method can rely on linking points in time for two electrodes and in turn generate a swept surface that can defines, at least in part, a volume. For example, linear, spline, or polynomial interpolation can generate a path between like time points on different electrodes of a multi-electrode lead or catheter. Motion of such an interpolated path can create a swept surface that bounds the trajectories of the electrodes used in its generation.

While the method 1000 relies on LEs, other techniques exist to determine a RE. For example, minimum and maximum points or ED and ES points for two or more electrodes can be used to create a bounding plane or volume. As described herein, electrodes may be optionally grouped when they are on the same lead or catheter or when they are in generally the same region of the cardiac space, for example electrodes on two different catheters at approximately the same level of different branches of the coronary sinus.

An exemplary method may rely on a parameterized surface (e.g., a circle or oval swept across an arc path perpendicular to its face, or a fraction of a torus, or a stacked series of truncated cones or cylinders, etc.) as a geometric model where defining parameters are computed by regression to find a best-fit surface or volume where such a surface or volume can include a number of sampled position points from trajectories of one or more electrodes.

As described herein, extended, linked, swept, extruded, or parameterized surface can define a bounding region where the volume of the bounded region may be determined. As mentioned, volume, linear dimension, aspect ratio, etc., of one or more bounding regions can provide valuable information related to myocardial performance. Further, surface area of an extended, linked, swept, extruded, or parameterized surface can provide an estimate of myocardial motion.

An exemplary method can analyze RE and determine myocardial properties. For example, referring to the damage zones of the heart 102 of FIG. 6, REs may be analyzed for various electrode pairs to identify damaged and healthy myocardium. When such analyses are performed over time, progression of damage or healing of the myocardium may be indicated by REs.

As described herein, one or more REs may be analyzed with respect to synchrony or dyssynchrony. For example, if position samples from like points in a cardiac cycle are connected for several electrodes to create a swept surface, and the surface so defined happens to be self-intersecting, a situation of two or more electrodes' motion being out of phase is indicated. In such a scenario, a pacing configuration that prevents the swept surface from intersecting itself may be considered in an effort to restore synchrony to the affected region of the heart. A self-intersecting surface can be identified by existence of a singularity, which can be detected by an algorithm and provide a alert (e.g., to a clinician during implantation of a lead).

FIG. 11 shows an exemplary RE method 1100 that exhibits dyssynchrony along with a plot 1120 of data points versus distance traversed with respect to a cardiac cycle. In the plot 1120, it can be seen that the distance covered by each respective electrode and the corresponding velocities of the electrodes differ; such differences alone can indicate dyssynchrony. The data in the method 1100 and the plot 1120 may be acquired using gating based on a feature in a cardiac cycle or an event (e.g., a time of paced stimulation, a sensing window, etc.). Where a common time reference exists between the electrode distance data comparisons may be made to determine whether a region, defined at least in part by the electrodes LV5 and LV-tip, exhibits synchrony or dyssynchrony. Referring again to the method 1100, a connection technique is used to connect points based on ED and ES for two electrodes. A resulting swept surface or volume (RE) exhibits twisting or conical cylindrical sections that are joined (i.e., two intersecting cones). The surface or volume can be indicative of dyssynchrony.

Figure 12:
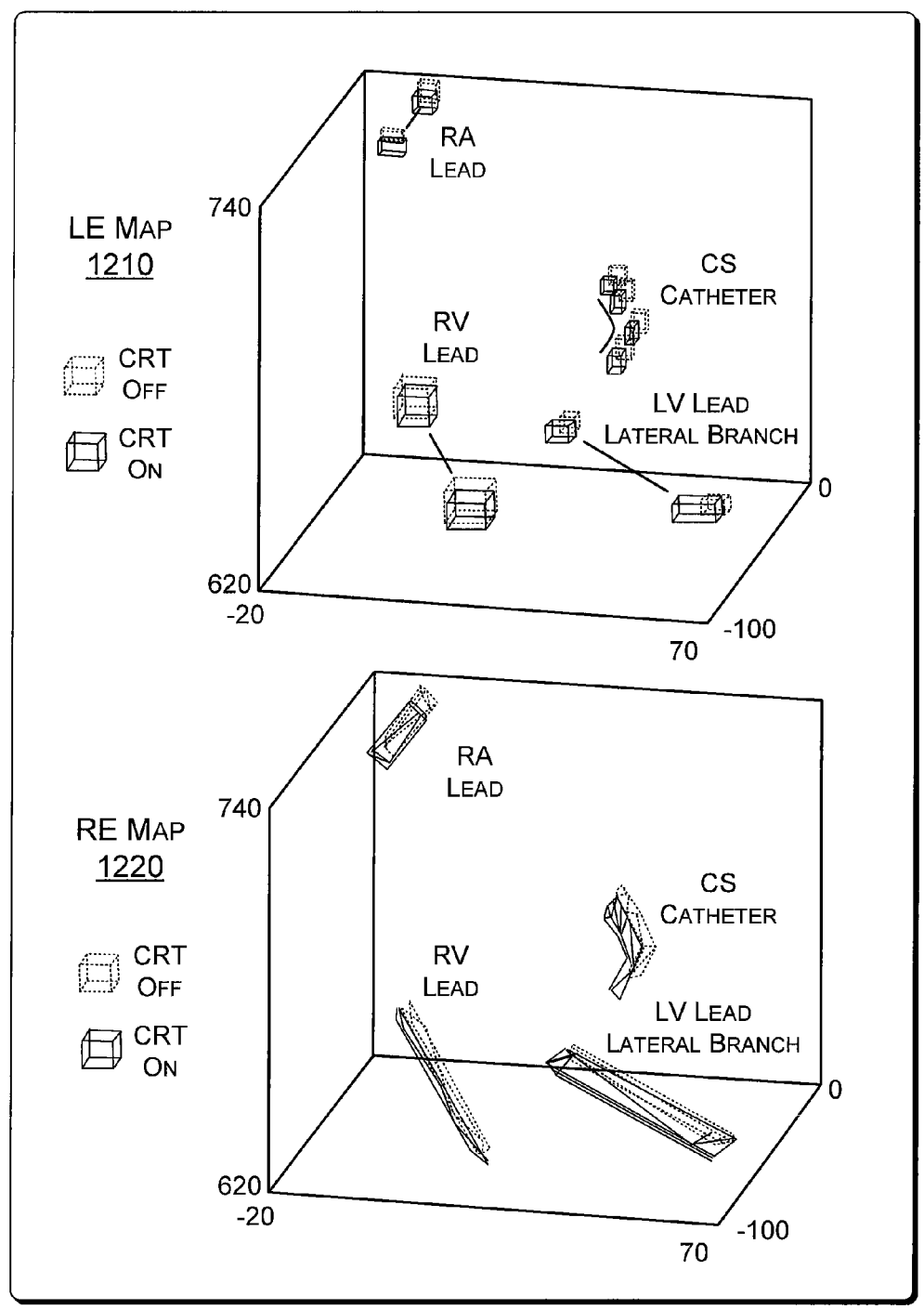
FIG. 12 is a series of plots, one for local estimators and one for regional estimators with a cardiac resynchronization therapy disabled and enabled.

FIG. 12 shows a local estimator map 1210 and a regional estimator map 1220 based on trial data. In this acute trial, a RA lead, a RV lead, a LV lead and a coronary sinus catheter were positioned and data acquired for two conditions: CRT off (dashed lines) and CRT on (solid lines). The local estimator map 1210 shows the "volume" of motion of each mapped electrode for both conditions. As indicated at the LV lead, the volume for each of the local estimators with CRT "on" is greater than the volume for each the local estimators with CRT "off". The 3-D local estimator map 1210 quickly allows a clinician to assess a condition, generally by comparing local estimators. While two conditions may be compared, a comparison may also occur between sites, for example, more movement occurs at the RV lead electrode sites than the CS catheter electrode sites as indicated by the local estimator volume being greater at the RV lead electrode sites than at the CS catheter electrode sites.

The regional estimator map 1220 generally shows volume swept by the respective leads or catheter for the two different conditions (CRT off/on). In the example of FIG. 12, the regional estimator map 1220 allows a clinician to readily assess how regions of the heart may be moving in response to CRT. For example, in response to CRT, one of the LV lead electrodes may move differently in comparison to another one of LV lead electrodes whereas without CRT the two electrodes move similarly. The regional estimators in the map 1220 can indicate such behavior, for example, via conical or other shapes that may exhibit twisting, bending, etc.

Figure 13:
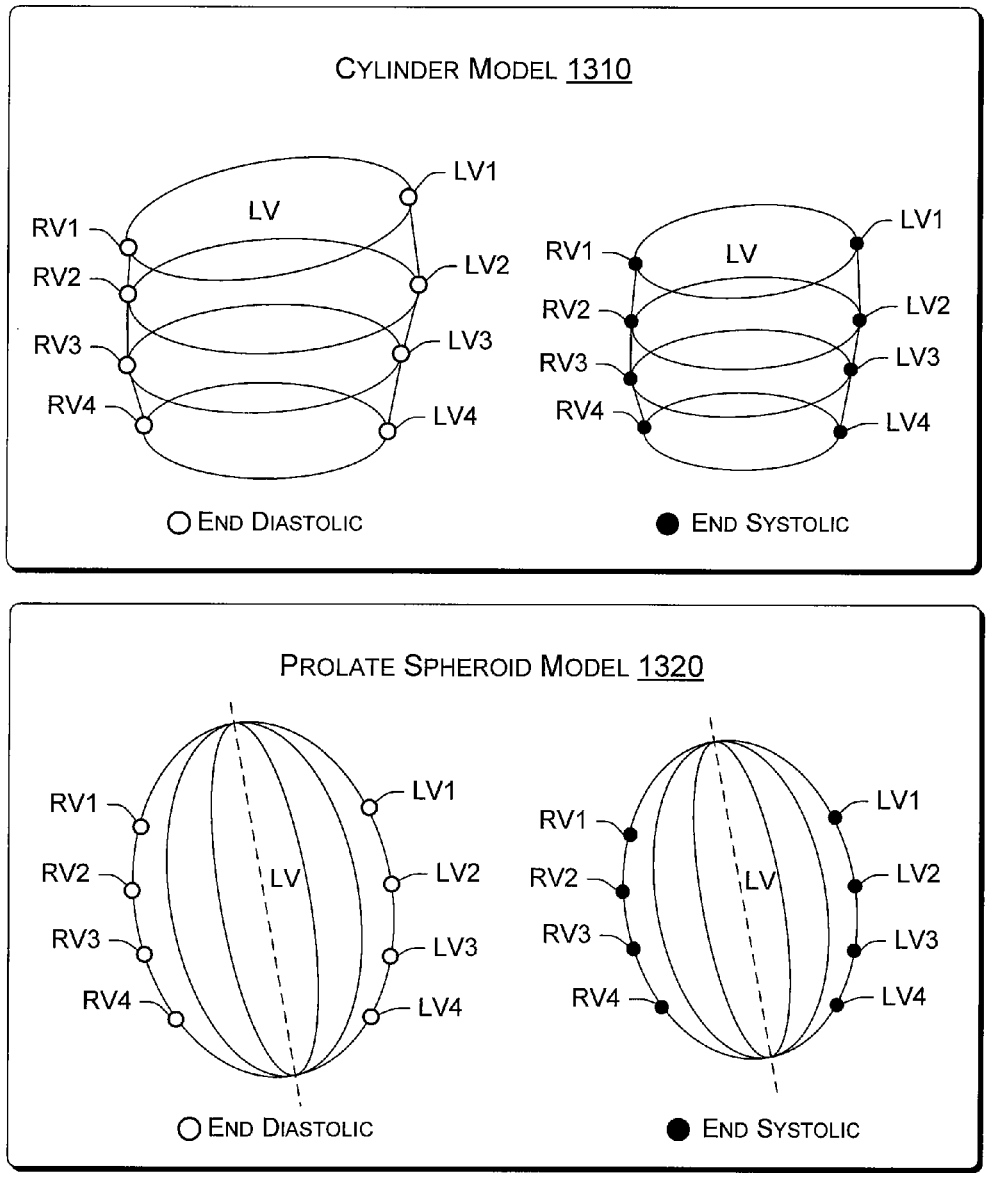
FIG. 13 is a representation of the left ventricle of the heart that includes a regional estimator based on electrodes located in the right ventricle (e.g., at or near the septum) and a FIG. 14 is a representation of the left ventricle that includes trajectories between the end systolic position of a right ventricular tip electrode and various end systolic positions of other electrodes.

FIG. 13 shows an exemplary method 1300 for determination of global estimators (GEs) with respect to a cylinder model 1310 and with respect to a prolate spheroid model 1320 according to information for various RV electrodes (RV1-RV4) and various LV electrodes (LV1-LV4).

Unlike the local estimators and regional estimators described above, global estimators use electrode motion information to extrapolate parameters that resemble physiologic cardiac volumes (e.g., left ventricular volume). For these estimators, a greater number of electrodes greatly increase the accuracy of the parameter estimates. Of particular interest are the end diastolic (ED) and end systolic (ES) points for volume estimation, which are shown with respect to each of the models 1310 and 1320. For example, from global estimators for ED and ES, parameters of clinical relevance such as end diastolic volume (EDV), end systolic volume (ESV), stroke volume, and ejection fraction (e.g., EF %=((EDV−ESV)/EDV)) can be determined.

Volumes of interest tend to generally be left ventricular volumes for the purpose of CRT optimization; however, given an appropriate electrode configuration with sufficient number of electrodes, other chamber volumes can be estimated. In the case of LV volumes, an RV-Tip electrode may generally be assumed to be on or near the interventricular septum, whether at the apex or outflow tract, as alternative locations for the RV lead (see, e.g., the RV lead 105 of FIG. 9). Hence, as described with respect to FIG. 13, information acquired for electrodes of the RV lead 105 can be combined with information for electrodes of the LV lead 107 to determine LV estimators.

As shown in FIG. 13, a general chamber geometry can be assumed (per the cylinder model 1310, the prolate spheroid model 1320 or other model), and appropriate parameters such as minor axis length or major axis length can be estimated from the distance between electrodes on the ventricular septum and free wall. Global estimators can be related to echocardiographic estimates of volume (e.g., using a paraboloid, ellipsoid, spheroid, or bullet model approximating LV shape). For ease of comparison and analysis, an exemplary method may rely on the same or similar shapes as an echocardiographic technique.

An exemplary method may rely on a general chamber geometry that defines a parameterized surface, for example an ellipsoid or a swept spline surface. According to such a method, end diastolic surfaces and end systolic surfaces can be determined as best-fit surfaces from the end diastolic points and the end systolic points of several electrodes. In this example, the parameterized surface itself is estimated by best-fit, rather than by simply assuming that interelectrode distances estimate axis dimensions. Hence, given a reasonable geometry assumption, the volume enclosed by the best-fit surface can be an as accurate (or more accurate) representation of a physiologic volume as a volume enclosed by an axis-dimension-defined surface of the same shape. While such an approach can be more computationally intensive, given the limited number of anticipated electrodes and a well-posed computational problem with properly defined constraints and boundary conditions, determinations may be provided in near real-time (e.g., within milliseconds).

As described herein, a GE may be determined based on positions of several electrodes, which in turn define a surface or a volume. Such an approach may optionally rely on a model, which may infer an assumed geometry such as cylinder or spheroid. In turn, positions of several electrodes may be used and a best-fit computed using the model geometry, for example, to minimize the sum square-distance between the model geometry surface and the electrode locations.

Another exemplary approach can include creating segments of a particular geometric shape. For example, a series of discs can be created for end diastole (ED) and end systole (ES) where each disc corresponds to a level along a long axis (e.g., major axis) of one or more electrodes. Such an approach may be formulated to facilitate comparison with information acquired using echocardiography (e.g., where volume can be estimated by "method of discs", consider the cylinder model 1310 where an overall cylinder is composed of discs).

In a disc approach, a short axis (e.g., minor axis) length can be taken as the diameter of a cylindrical disc. Accordingly, a volume of a stack of discs approximates chamber volume. Such an approach is particularly suited to scenarios where multi-electrode leads or catheters are positioned on both the free wall of the left ventricle and on the septum; noting that projection of ED points and ES points of a single electrode can be used to estimate the location of a "hypothetical electrode" at the level of a disc. Further, it can be expected that electrodes in multiple coronary sinus branches can provide a better estimate of disc size than a single branch alone, by providing chords of each disc in addition to simply approximating diameter.

Referring to the previous three embodiments, the same information can be reduced to provide other estimates of volume-type parameters. For example, a two-dimensional correlate of ejection fraction is fractional area change (FAC %), defined as the difference between end diastolic area (EDA) and end systolic area (ESA), divided by end diastolic area (FAC %=((EDA−ESA)/EDA)). Similarly, a one-dimensional correlate of ejection fraction is fractional shortening (FS %), defined as the difference in end diastolic chamber diameter (EDD) and end systolic chamber diameter (ESD), divided by end diastolic diameter (FS %=((EDD−ESD)/EDD)). Both of these parameters are used in echocardiography and can be determined using various electrode tracking techniques described herein.

Figure 14:
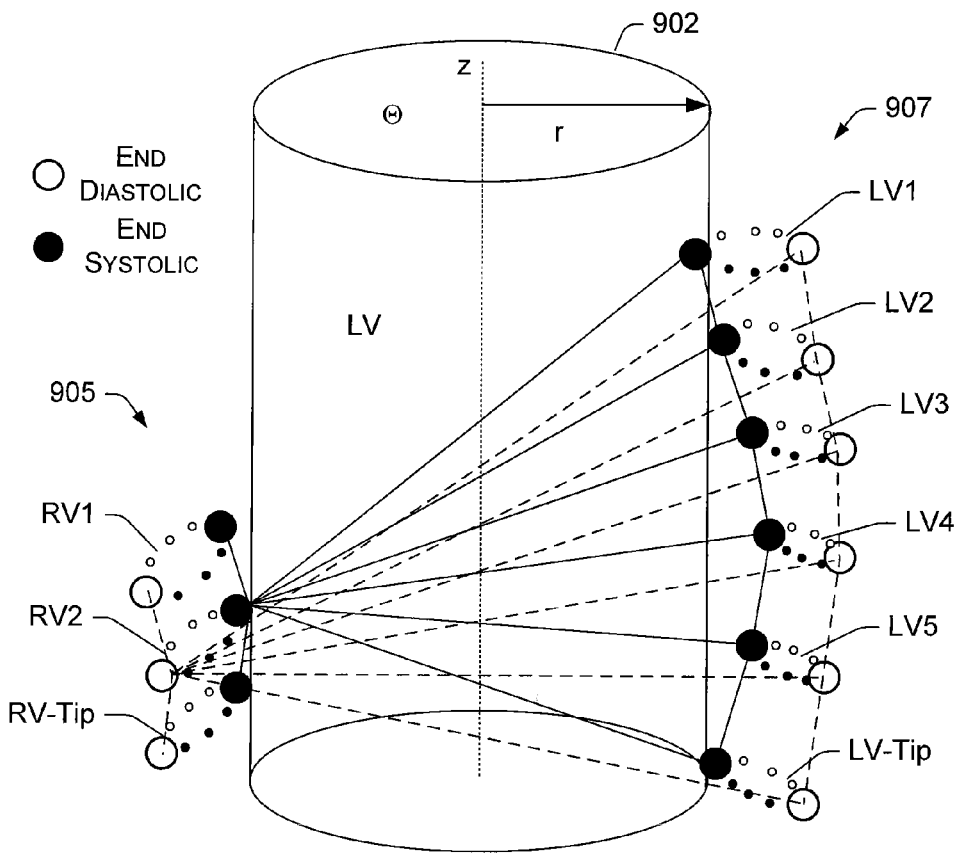

FIG. 14 shows an exemplary mesh-trajectory method 1400 with reference to the cylinder model 902 and end diastolic (ED) points and end systolic (ES) points for electrodes of the right ventricular lead 105 and for electrodes of the left ventricular lead 107 (where points are labeled 905 and 907, respectively); noting that such a method does not necessarily require a cylinder model or other particular geometric model.

According to the method 1400, segments may be introduced that connect positions of various electrodes. In the example of FIG. 14, the ES point of the right ventricular lead electrode RV2 is shown with segments to ES points of all other electrodes. When many segments are introduced, a mesh is created that links the positions. As described herein, global volume estimation may rely on construction of a mesh (e.g., a "wireframe" or "skeleton"). For example, such a mesh may be constructed by setting each electrode position as a node and connecting various nodes with path segments. In such an exemplary approach, outermost segments of a mesh can define a boundary of the left ventricular chamber and the volume of the left ventricle can then be determined.

The mesh-trajectory approach can also analyze change in length of given segments, for example, from ED points to ES points, which may indicate local or regional strain. An exemplary method may update a mesh at every sample point throughout the cardiac cycle, and volumetric measures of the mesh-enclosed chamber can be made at any gated point in the cycle, including the points of maximum and minimum volume or the points corresponding to end diastole (ED) and end systole (ES).

In general, computational complexity increases exponentially as number of electrodes/nodes increases. As such, several methods for reducing this complexity can be implemented. A fraction such as ½, ⅓, or ¼ of the total possible number of segments may be drawn/computed at one sample point or cardiac cycle, and then the complementary fraction (s) of segments can be drawn/computed at subsequent sample points or cardiac cycles. In like manner, a fraction of the possible number of nodes may be used at one sample point or cardiac cycle, and the complementary nodes used in subsequent sample points or cardiac cycles. The wireframe volumes can then be averaged or summed across a number of cycles to estimate the total.

Preferably, the number and type of segments between any two nodes can be governed by a set of rules based on a defined "class" or "group", which an electrode belongs. For example, several electrodes on a single lead or catheter can only be connected to their immediate neighbors on that lead or catheter, reducing the complexity and number of segments needed to define a single lead or catheter. Similarly, two leads or catheters in branches of the coronary sinus might be connected by only a few segments per electrode (e.g., corresponding to electrodes at approximately the same level of the chamber).

As described herein, acquisition of position information for electrodes may occur during a single cardiac cycle or during multiple cardiac cycles. Specifically, in various examples, position information for some electrodes many be acquired during a first cardiac cycle and position information for other electrodes acquired during a subsequent cardiac cycle.

As described herein, position information may also be acquired for each of a variety of electrode locations, the locations achieved by maneuvering one or more electrodes. Given such information, an estimator can be determined for each location of an electrode, where such determinations may be gated to a cardiac cycle or trajectory, as described above. Such a technique may operate in a manner as if the points had instead been collected from separate electrodes at the same time or cardiac cycle. Such point-by-point motion mapping can advantageously reduce the number of electrodes necessary to obtain data sufficient to compute a volumetric type parameter.

As described herein, point-by-point mapping may be achieved in the endocardial or intrapericardial space by maneuvering a lead or catheter electrode to a location in contact with the heart wall, maintaining the electrode location for at least one cardiac cycle while recording the motion of the electrode coupled to the myocardial motion, and then moving the electrode to other locations, recording motion at each.

Point-by-point mapping may be achieved in the transvenous space by recording the motion of one or more electrodes on a lead or catheter as it is advanced into the coronary sinus and down one or more branches, as well as by locating the lead or catheter at a distal portion of the coronary sinus or branch thereof and subsequently retracting the lead or electrode more proximally; in either case, the maneuvering of the lead or catheter can be paused periodically for one or more cardiac cycles to allow for recording of cardiac-coupled electrode motion from each respective location in the cardiac space.

An exemplary method can include point-by-point mapping while a patient exhibits a stable rhythm, for example sinus rhythm. Such mapping can be then used as a baseline. According to such a method, a clinician can maneuver one or more catheters to achieve the point-wise data collection while keeping location of one or more other catheters fixed. Such a point-by-point mapping can then be repeated while pacing from one or more of the fixed-location catheters, such that the pacing locations remain the same while the patient exhibits a stable rhythm.

In an alternative approach, a clinician may choose to acquire position information for both establishing a sinus rhythm baseline and for determining the effects of pacing without maneuvering any electrodes. In turn, after acquisition of sufficient position information, the clinician may reposition (i.e., maneuver) one or more electrodes and repeat the acquisition process. In such an approach, volumetric data can be assigned for each collected point to a respective map corresponding to a pacing intervention under investigation.

In yet another approach for point-by-point mapping, a set of fixed-location electrodes can be used to acquire position information sufficient for generation of one or more estimators, while one or more maneuvering leads or catheters are used to pace from different locations. In this approach, estimators can be determined for a baseline and can be determined while pacing from each location. Such an approach provides for comparison with respect to the choice of local, regional, or global estimators, while maneuvering a pacing catheter. Results from such a study can be used to select an optimal location or locations for delivery of a pacing therapy.

Another exemplary method for point-by-point mapping includes maneuvering one or more catheters to various locations of the heart. At each location, position information sufficient to determine one or more estimators can be acquired for a baseline state and for one or more pacing states, defined while pacing from one or more electrodes of maneuvering catheter. In this example, estimators may be presented as "deltas" that represent the change in value of a local or regional estimator at any given location at baseline versus pacing from that same location. Such a technique can yield valuable information about functional properties of the local tissue itself.

Figure 15:
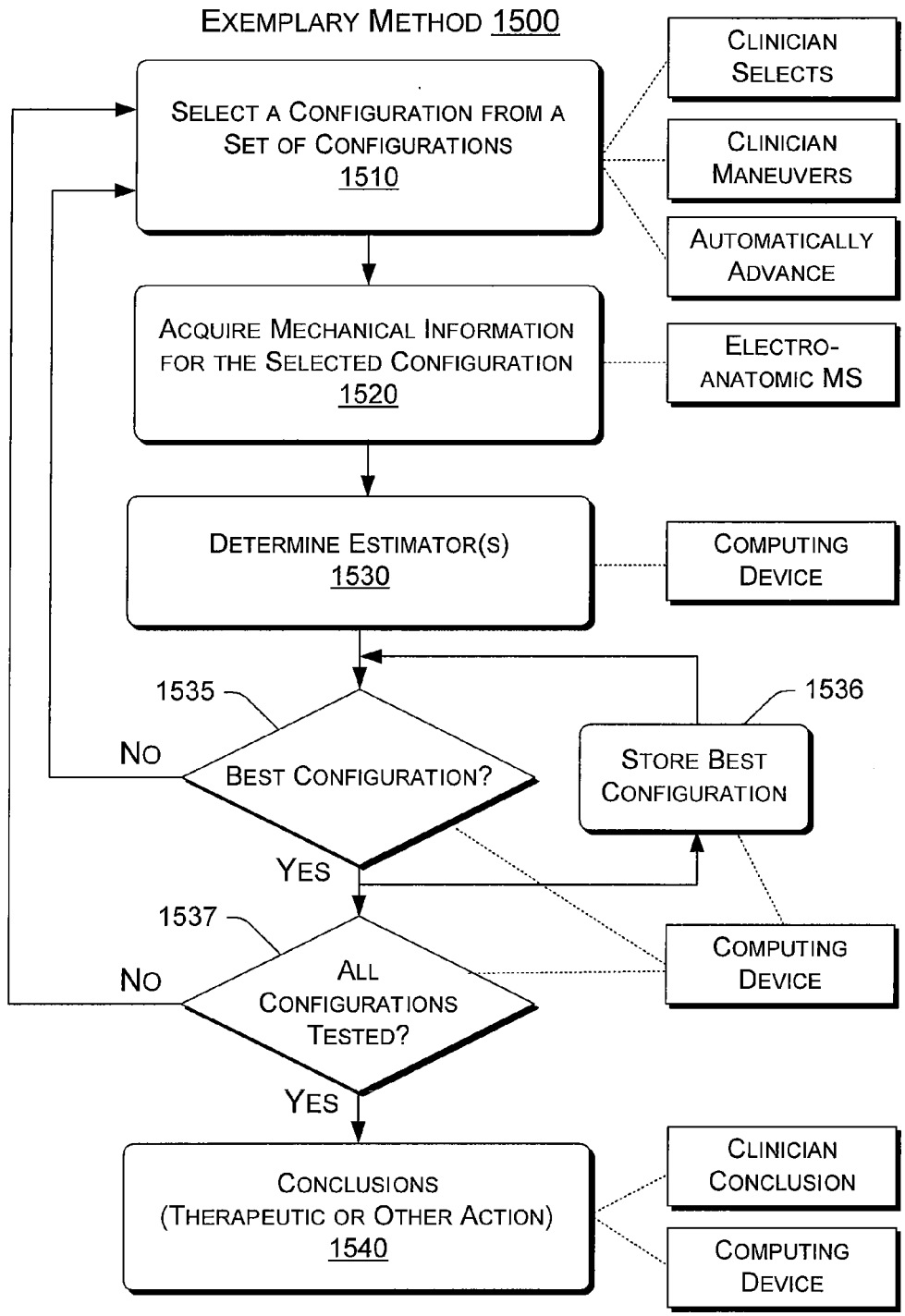
FIG. 15 is a block diagram of an exemplary method for selecting a best configuration for delivery of a cardiac pacing therapy.

FIG. 15 shows an exemplary method 1500 for determining a best configuration for delivery of a pacing therapy. Such a method may be implemented in near real-time given sufficient equipment. As described herein, near real-time corresponds to an acceptable time for an intraoperative environment where a clinician may maneuver an electrode-bearing catheter or an electrode-bearing lead in a patient to a location and then decide, based on information acquired corresponding to the location, whether another location should be examined. In general, such a process occurs iteratively and an acceptable time for acquisition of information and processing of the acquired information to produce a result can be on the order of several minutes, which, of course, depends on the underlying computing resources (e.g., memory, processors, GPU(s), etc.).

A clinically acceptable period of time may be, for example, up to 10 minutes. To produce meaningful results, however, only a handful of paced beats for each configuration may be needed to test a configuration, which would correspond to a time of approximately 1 to 2 minutes for a conventional CRT system or, for example, up to approximately 5 minutes for a CRT system with a quadpolar LV lead and possibly one or more LA electrode(s) (assuming multisite stimulation would be tested among various possible configurations).

An exemplary technique may rely on results for one or a few configurations to forego testing of one or more other configurations. Such a technique may shorten optimization time to optimize configuration, for example, based on application of results to one or more rules.

As shown in FIG. 15, the method 1500 includes a selection block 1510 where a configuration is selected from a set of configurations. Such configurations may be achieved by maneuvering an electrode in a patient and/or by other techniques (e.g., adjusting a pacing voltage, adjusting electrode polarity, adjusting timing of a pulse, etc.). Next, an acquisition block 1520 acquires mechanical information for the selected configuration. Acquisition may occur using an electroanatomic mapping or locating system (e.g., ENSITE® NavX system or other system). Such acquisition may occur without pacing (e.g., to establish a baseline) and/or with pacing (e.g., to examine the effects of a configuration). Once sufficient mechanical information has been acquired, a determination block 1530 determines one or more estimators based at least in part on the acquired mechanical information. Such a determination may be made by a computing device associated with the electroanatomic system or a computing device otherwise configured (e.g., hardware and software) of making such determinations based on acquired mechanical information. A decision block 1535 follows that decides if the selected configuration per the selection block 1510 is the best configuration (e.g., better than others tested). Such a decision may rely on information about a previous "best" configuration (e.g., per a storage block 1536). Such a decision may rely on objective factors (e.g., EF, lack of dyssynchrony, etc.) and/or subjective factors (e.g., how a patient "feels", etc.).

If the decision block 1535 decides that the selected configuration is not the "best", then the method 1500 continues at the selection block 1510 where another configuration is selected from the set of configurations. However, if the decision block 1535 decides that the selected configuration is the "best", then the method 1500 enters the storage block 1536 that stores the best configuration (e.g., the best configuration, information about the best configuration, etc.). In turn, another decision block 1537 follows that decides if all of the configurations in the set of configurations have been selected and tested. If so, then the method 1500 enters a conclusion block 1540; otherwise, the results (e.g., one or more estimators) are stored and another configuration is selected per the selection block 1510. As shown, one or more computing devices may be configured to perform various actions of the method 1500. Details of a data acquisition and computing environment are described with respect to the system 1600 of FIG. 16.

As mentioned, an exemplary method may act to optimize in a manner that avoids a need to test all configurations. For example, in the method 1500 of FIG. 15, in the decision block 1537, rather than deciding whether all configurations are tested, the decision block may decide whether a sufficient number of configurations have been tested (e.g., sufficient to further optimize or ultimately arrive at an optimal result such as "use configuration X"). In such a scenario, the method 1500 the decision block 1535 and other portions may be modified accordingly.

As explained, various exemplary systems and methods can provide for near real-time guidance of CRT implants based on estimators. Various estimators described herein are based at least in part on electrode trajectories or particular points along those trajectories. Volume being a real, physical, and intuitive quantity, the presentation of a volume estimator can influence a clinician's perception and facilitate choosing an optimal pacing configuration.

A brief discussion of several ways to report estimators in near real-time follows, describing some possible ways to represent the estimators usefully; noting that other reporting formats for these estimators exist and may be used, as appropriate or desired.

As with any physiologic parameter, the value of an estimator may be displayed as a streaming waveform, or end diastolic (ED) and end systolic (ES) gated parameters of volume estimation may be displayed as a scatter plot or histogram. Flags, labels, symbols, or colors may be used to delineate different pacing configurations, for example using a different color in a scatter plot for each different timing interval. Further, the beat-wise value of an estimator or a running average, max, or min, can be reported in a digital display.

For some clinicians, a graphical representation may prove more useful than a waveform or digital display of estimators. For each estimator, a graphics window can be updated in near real-time, either in streaming mode or in gated mode, to show the bounding volumes, swept or extruded surfaces, best-fit geometries, or wireframes, as appropriate. In such an example, graphical renderings can be part of an interactive user interface where a clinician can pan, rotate, and zoom in real-time to fully appreciate the estimators. An additional benefit of this feature is that debugging, such as noting faulty electrodes, poor signal quality, or mistaken connections, may be more easily detected and corrected than with waveform or digital display. Further, separate scale factors can be defined for each axis or for various regions of the cardiac space.

As mentioned, estimators may be local, regional or global. A local estimator typically corresponds to a point, as represented by movement of a single electrode or a closely spaced electrode pair. In various examples, the path of an electrode in time (e.g., over a cardiac cycle), may be represented as an orbit, a surface or, in 3D, a volume. A regional estimator corresponds to two or more points, for example, as represented by two adjacent electrodes spaced along a lead. In various examples, the paths of two points in time (e.g., over a cardiac cycle) may be used to sweep a surface that encloses, at least in part, a volume or may be used to extrude a volume. A global estimator corresponds to at least two or three points with a model (e.g., depending on the model and associated constraints) or, without a model, four or more points (e.g., consider a volume such as a tetrahedron). For example, a global estimator may pertain to the left ventricle of a patient, optionally relying on a model such as a cylinder model, a cone model or a prolate spheroid model. With respect to a change in volume, position information for two electrodes at two different points in time may be sufficient to infer a volume changes give a model (e.g., consider the model 1320 of FIG. 13 where a prolate spheroid model with a constrained axis may be used to determine a volume for two points at any given time).

As described herein, local, regional and global estimators may be used in various manners to aid in diagnosing cardiac conditions. Local and regional estimators provide information about wall motion and contractility. An exemplary method can select an electrode configuration for pacing the heart that maximizes wall motion, contractility or a combination of both. Such a routine may act to ensure that dyssynchrony is minimized or, in other words, that synchrony is maximized (e.g., for the myocardium responsible for operation of the left ventricle).

Global estimators can provide information about changes in volume of a chamber of the heart. An exemplary method can select an electrode configuration for pacing the heart that optimizes volume of the left ventricle. For example, an optimization routine may rely on global estimators of volume to reduce end diastolic volume, to increase ejection fraction or to reduce end diastolic volume and to increase ejection fraction. Such a method may optionally rely on one or more local estimators, one or more regional estimators or a combination of one or more local estimators and one or more regional estimators. For example, the optimal volume may correspond to an electrode configuration and associated pacing parameters that optimize left ventricular volume while achieving an acceptable degree of synchrony between the septal wall and the lateral wall of the left ventricle. With respect to the associated pacing parameters, these may include parameters relating to polarity, timing, duration, waveform, amplitude, energy, etc.

As described herein, one or more estimators can aid in diagnosing ischemia or tissue viability. Ischemia pertains to a restriction of blood flow or the perfused state of tissue. For example, tissue that is not receiving oxygenated blood is likely to become kinetically impaired. Tissue viability pertains to the state of tissue, for example, scarred, damaged, healing, healthy, etc. In general, scar tissue or dead tissue is akinetic, i.e., does not respond to any significant degree to an electrical stimulus. However, akinetic tissue may still move in response to movement of adjacent kinetic tissue (e.g., by being teathered to responsive myocardial tissue). Tissue with slow conduction or even healthy tissue may be diskinetic. An analysis of local estimator kinetics may help identify tissue that is akinetic, kinetic or diskinetic. Further, local estimators may help diagnose tissue state. Regional estimators, alone or in combination with one or more other estimators, may help in such identifications or diagnoses.

As described herein, global estimators may help diagnose cardiac conditions such as dilated cardiomyopathy. Dilated cardiomyopathy (DCM), also known as congestive cardiomyopathy, is a condition in which the heart becomes weakened and enlarged, and cannot pump blood efficiently. Global estimators over a cardiac cycle may indicate that a heart is enlarged and that the ejection volume or ejection fraction is low. Such a diagnosis may be bolstered by an examination of one or more local estimators, one or more regional estimators or a combination of one or more local estimators and one or more regional estimators. For example, a local estimator that does not sweep a path having an area greater than a predetermined value may indicate that the tissue is weak or thin, which are conditions indicative of DCM. Similarly, a regional estimator that does not sweep a surface or define a volume greater than a predetermined value may indicate that the corresponding tissue of the region is weak or thin.

As described herein, local, regional and global estimators may be acquired during an acute phase or, depending on capabilities, during a chronic phase. During an acute phase (intraoperative phase), factors such as electrode placement can be prioritized as other parameters may be optionally optimized in a chronic phase (post-operative phase). With respect to acquisition during a chronic phase, patches may be placed on the body of a patient to generate one or more current fields. In turn, an implanted device may sense potentials associated with the one or more current fields. The sensed potentials may be analyzed by the implanted device or communicated to an external device that can analyze the sensed potentials. Based on the sensed potentials, an analysis may determine one or more estimators (e.g., one or more of local, regional and regional estimators). After such an analysis, one or more pacing parameters may be set or adjusted to improve cardiac performance.

Exemplary External Programmer

Figure 16:
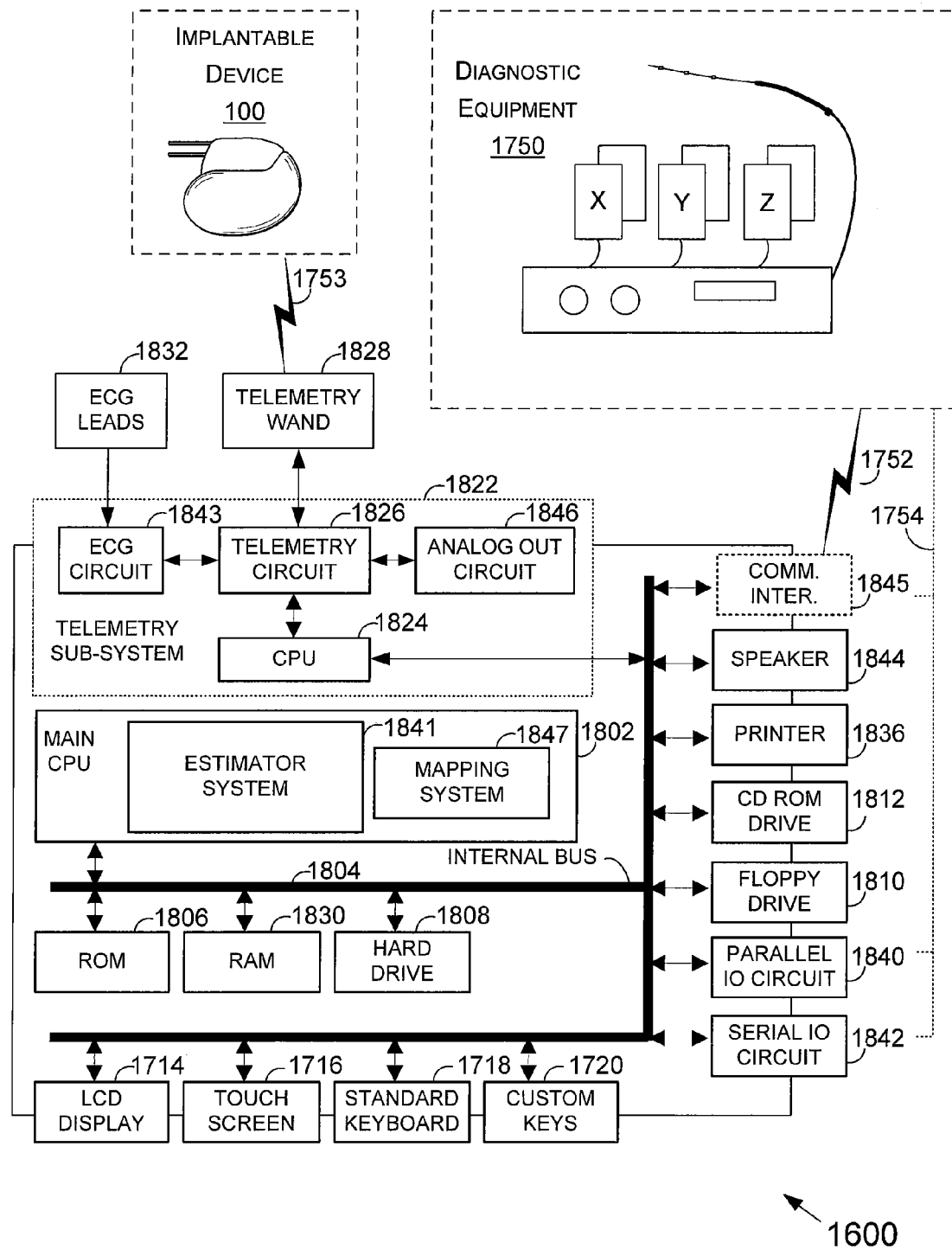
FIG. 16 is an exemplary system for acquiring information and analyzing such information.

FIG. 16 illustrates pertinent components of an external programmer 1600 for use in programming an implantable medical device 100 (see, e.g., FIGS. 1 and 2). The external programmer 1600 optionally receives information from other diagnostic equipment 1750, which may be a computing device capable of acquiring motion information related to cardiac mechanics. For example, the equipment 1750 may include a computing device to deliver current and to measure potentials using a variety of electrodes including at least one electrode positionable in the body (e.g., in a vessel, in a chamber of the heart, within the pericardium, etc.). Equipment may include a lead for chronic implantation or a catheter for temporary implantation in a patient's body. Equipment may allow for acquisition of respiratory motion and aid the programmer 1600 in distinguishing respiratory motion from cardiac.

Briefly, the programmer 1600 permits a clinician or other user to program the operation of the implanted device 100 and to retrieve and display information received from the implanted device 100 such as IEGM data and device diagnostic data. Where the device 100 includes a module such as the motion module 239, then the programmer 1600 may instruct the device 100 to measure potentials and to communicate measured potentials to the programmer via a communication link 1753. The programmer 1600 may also instruct a device or diagnostic equipment to deliver current to generate one or more potential fields within a patient's body where the implantable device 100 may be capable of measuring potentials associated with the field(s).

The external programmer 1600 may be configured to receive and display ECG data from separate external ECG leads 1832 that may be attached to the patient. The programmer 1600 optionally receives ECG information from an ECG unit external to the programmer 1600. As already mentioned, the programmer 1600 may use techniques to account for respiration.

Depending upon the specific programming, the external programmer 1600 may also be capable of processing and analyzing data received from the implanted device 100 and from ECG leads 1832 to, for example, render diagnosis as to medical conditions of the patient or to the operations of the implanted device 100. As noted, the programmer 1600 is also configured to receive data representative of conduction time delays from the atria to the ventricles and to determine, therefrom, an optimal or preferred location for pacing. Further, the programmer 1600 may receive information such as ECG information, IEGM information, information from diagnostic equipment, etc., and determine one or more estimator (e.g., consider the method 300).

Now, considering the components of programmer 1600, operations of the programmer are controlled by a CPU 1802, which may be a generally programmable microprocessor or microcontroller or may be a dedicated processing device such as an application specific integrated circuit (ASIC) or the like. Software instructions to be performed by the CPU are accessed via an internal bus 1804 from a read only memory (ROM) 1806 and random access memory 1830. Additional software may be accessed from a hard drive 1808, floppy drive 1810, and CD ROM drive 1812, or other suitable permanent or removable mass storage device. Depending upon the specific implementation, a basic input output system (BIOS) is retrieved from the ROM 1806 by CPU 1802 at power up. Based upon instructions provided in the BIOS, the CPU 1802 "boots up" the overall system in accordance with well-established computer processing techniques.

Once operating, the CPU 1802 displays a menu of programming options to the user via an LCD display 1714 or other suitable computer display device. To this end, the CPU 1802 may, for example, display a menu of specific programming parameters of the implanted device 100 to be programmed or may display a menu of types of diagnostic data to be retrieved and displayed. In response thereto, the clinician enters various commands via either a touch screen 1716 overlaid on the LCD display or through a standard keyboard 1718 supplemented by additional custom keys 1720, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

With regard to the determination of the optimal pacing location, CPU 1802 includes an estimator system 1841 and a 3-D mapping system 1847. The systems 1841 and 1847 may receive mechanical information and electrical information or other information from the implantable device 100 and/or diagnostic equipment 1750. The estimator system 1841 optionally includes control logic to associate information and to make one or more conclusions based on an estimator (e.g., consider the LEs, REs and GEs of block 330 of FIG. 3). As shown in FIG. 16, control logic associated with one or more components or modules may be, in part, in the form of processor-executable instructions embodied in one or more processor-readable media (e.g., consider a computer-readable medium such as a storage medium that may be read into memory). Hence, the CPU 1802 or the CPU 1824 may implement control logic. Control logic may be in the form of circuitry, instructions or a combination of circuitry and instructions. Various methods described herein may be implemented, at least in part, by control logic (e.g., in a system such as the system 1600).

Where information is received from the implanted device 100, a telemetry wand 1828 may be used. Other forms of wireless communication exist as well as forms of communication where the body is used as a "wire" to communicate information from the implantable device 100 to the programmer 1600.

If information is received directly from diagnostic equipment 1750, any appropriate input may be used, such as parallel IO circuit 1840 or serial IO circuit 1842. Motion information received via the device 100 or via other diagnostic equipment 1750 may be analyzed using the mapping system 1847. In particular, the mapping system 1847 (e.g., control logic) may identify positions within the body of a patient and associate such positions with one or more electrodes where such electrodes may be capable of delivering stimulation energy to the heart.

A communication interface 1845 optionally allows for wired or wireless communication with diagnostic equipment 1750 or other equipment. The communication interface 1845 may be a network interface connected to a network (e.g., intranet, Internet, etc.).

A map or model of cardiac motion may be displayed using display 1714 based, in part, on 3-D heart information and optionally 3-D torso information that facilitates interpretation of motion information. Such 3-D information may be input via ports 1840, 1842, 1845 from, for example, a database, a 3-D imaging system, a 3-D location digitizing apparatus (e.g., stereotactic localization system with sensors and/or probes) capable of digitizing the 3-D location. According to such an example, a clinician can thereby view the optimal location for delivery of stimulation energy on a map of the heart to ensure that the location is acceptable before an electrode or electrodes are positioned and optionally fixed at that location. While 3-D information and localization are mentioned, information may be provided with fewer dimensions (e.g., 1-D or 2-D). For example, where motion in one dimension is insignificant to one or more other dimensions, then fewer dimensions may be used, which can simplify procedures and reduce computing requirements of a programmer, an implantable device, etc. The programmer 1600 optionally records procedures and allows for playback (e.g., for subsequent review). For example, a heart map and all of the electrical activation data, mechanical activation data, VE data, etc., may be recorded for subsequent review, perhaps if an electrode needs to be repositioned or one or more other factors need to be changed (e.g., to achieve an optimal configuration). Electrodes may be lead based or non-lead based, for example, an implantable device may operate as an electrode and be self powered and controlled or be in a slave-master relationship with another implantable device (e.g., consider a satellite pacemaker, etc.). An implantable device may use one or more epicardial electrodes.

Once all pacing leads are mounted and all pacing devices are implanted (e.g., master pacemaker, satellite pacemaker, biventricular pacemaker), the various devices are optionally further programmed.

The telemetry subsystem 1822 may include its own separate CPU 1824 for coordinating the operations of the telemetry subsystem. In a dual CPU system, the main CPU 1802 of programmer communicates with telemetry subsystem CPU 1824 via internal bus 1804. Telemetry subsystem additionally includes a telemetry circuit 1826 connected to telemetry wand 1828, which, in turn, receives and transmits signals electromagnetically from a telemetry unit of the implanted device. The telemetry wand is placed over the chest of the patient near the implanted device 100 to permit reliable transmission of data between the telemetry wand and the implanted device.

Typically, at the beginning of the programming session, the external programming device 1600 controls the implanted device(s) 100 via appropriate signals generated by the telemetry wand to output all previously recorded patient and device diagnostic information. Patient diagnostic information may include, for example, motion information (e.g., cardiac, respiratory, etc.) recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like.

Data retrieved from the implanted device(s) 100 can be stored by external programmer 1600 (e.g., within a random access memory (RAM) 1830, hard drive 1808, within a floppy diskette placed within floppy drive 1810). Additionally, or in the alternative, data may be permanently or semi-permanently stored within a compact disk (CD) or other digital media disk, if the overall system is configured with a drive for recording data onto digital media disks, such as a write once read many (WORM) drive. Where the programmer 1600 has a communication link to an external storage device or network storage device, then information may be stored in such a manner (e.g., on-site database, off-site database, etc.). The programmer 1600 optionally receives data from such storage devices.

A typical procedure may include transferring all patient and device diagnostic data stored in an implanted device 100 to the programmer 1600. The implanted device(s) 100 may be further controlled to transmit additional data in real time as it is detected by the implanted device(s) 100, such as additional motion information, IEGM data, lead impedance data, and the like. Additionally, or in the alternative, telemetry subsystem 1822 receives ECG signals from ECG leads 1832 via an ECG processing circuit 1834. As with data retrieved from the implanted device 100, signals received from the ECG leads are stored within one or more of the storage devices of the programmer 1600. Typically, ECG leads output analog electrical signals representative of the ECG. Accordingly, ECG circuit 1834 includes analog to digital conversion circuitry for converting the signals to digital data appropriate for further processing within programmer 1600. Depending upon the implementation, the ECG circuit 1843 may be configured to convert the analog signals into event record data for ease of processing along with the event record data retrieved from the implanted device. Typically, signals received from the ECG leads 1832 are received and processed in real time.

Thus, the programmer 1600 is configured to receive data from a variety of sources such as, but not limited to, the implanted device 100, the diagnostic equipment 1750 and directly or indirectly via external ECG leads (e.g., subsystem 1822 or external ECG system). The diagnostic equipment 1750 includes wired 1754 and/or wireless capabilities 1752 which optionally operate via a network that includes the programmer 1600 and the diagnostic equipment 1750 or data storage associated with the diagnostic equipment 1750.

Data retrieved from the implanted device(s) 100 typically includes parameters representative of the current programming state of the implanted devices. Under the control of the clinician, the external programmer displays the current programming parameters and permits the clinician to reprogram the parameters. To this end, the clinician enters appropriate commands via any of the aforementioned input devices and, under control of CPU 1802, the programming commands are converted to specific programming parameters for transmission to the implanted device 100 via telemetry wand 1828 to thereby reprogram the implanted device 100 or other devices, as appropriate.

Prior to reprogramming specific parameters, the clinician may control the external programmer 1600 to display any or all of the data retrieved from the implanted device 100, from the ECG leads 1832, including displays of ECGs, IEGMs, statistical patient information (e.g., via a database or other source), diagnostic equipment 1750, etc. Any or all of the information displayed by programmer may also be printed using a printer 1836.

A wide variety of parameters may be programmed by a clinician. In particular, for CRT, the AV delay and the VV delay of the implanted device(s) 100 are set to optimize cardiac function. In one example, the VV delay is first set to zero while the AV delay is adjusted to achieve the best possible cardiac function, optionally based on motion information. Then, VV delay may be adjusted to achieve still further enhancements in cardiac function.

Programmer 1600 optionally includes a modem to permit direct transmission of data to other programmers via the public switched telephone network (PSTN) or other interconnection line, such as a T1 line or fiber optic cable. Depending upon the implementation, the modem may be connected directly to internal bus 1804 may be connected to the internal bus via either a parallel port 1840 or a serial port 1842.

Other peripheral devices may be connected to the external programmer via the parallel port 1840, the serial port 1842, the communication interface 1845, etc. Although one of each is shown, a plurality of input output (IO) ports might be provided. A speaker 1844 is included for providing audible tones to the user, such as a warning beep in the event improper input is provided by the clinician. Telemetry subsystem 1822 additionally includes an analog output circuit 1846 for controlling the transmission of analog output signals, such as IEGM signals output to an ECG machine or chart recorder.

With the programmer 1600 configured as shown, a clinician or other user operating the external programmer is capable of retrieving, processing and displaying a wide range of information received from the ECG leads 1832, from the implanted device 100, the diagnostic equipment 1750, etc., and to reprogram the implanted device 100 or other implanted devices if needed. The descriptions provided herein with respect to FIG. 16 are intended merely to provide an overview of the operation of programmer and are not intended to describe in detail every feature of the hardware and software of the device and is not intended to provide an exhaustive list of the functions performed by the device.

Conclusion

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method for selecting a position for an electrode for delivering cardiac pacing therapy, said method comprising:

providing three-dimensional position information, for at least two points in time of a cardiac cycle, for an electrode located at a first position in a cardiac space and determining a first local estimator for the electrode at the first position, wherein the first local estimator is a volume derived from the position information of the electrode at the first position;

providing three-dimensional position information, for at least two points in time of a cardiac cycle, for an electrode located at a second position in the cardiac space and determining a second local estimator for the electrode at the second position, wherein the second local estimator is a volume derived from the position information of the electrode at the second position;

comparing the first local estimator with the second local estimator to identify which of the first position or second position has the greater volume; and selecting the identified first position or the second position as the position for the electrode for delivering cardiac pacing therapy.

2. The method of claim 1 wherein one of the dimensions corresponds to a major axis of the heart.

3. The method of claim 1 wherein one of the dimensions corresponds to a minor axis of the heart.

4. The method of claim 1 each of the first local estimator and the second local estimator are based at least in part on a maximum position value and a minimum position value along one of the dimensions.

5. The method of claim 1 wherein each of the first local estimator and the second local estimator are based at least in part on a difference between a maximum position value and a minimum position value along one of the dimensions.

6. The method of claim 1 wherein the at least two points in time comprise an end diastolic time.

7. The method of claim 1 wherein the at least two points in time comprise an end systolic time.

8. The method of claim 1 wherein the electrode for the first local estimator and the electrode for the second local estimator comprise different electrodes.

9. The method of claim 1 further comprising diagnosing, based at least in part on the first local estimator and the second local estimator, a cardiac condition wherein the cardiac condition comprises a condition selected from a group consisting of ischemia, tissue viability, scarring, dyssynchrony and dilated cardiomyopathy.

10. The method of claim 1 wherein the selecting comprises summing a plurality of local estimators, computing a variance of a plurality of local estimators or computing a standard deviation of a plurality of local estimators.

11. A method for selecting a pacing scheme for delivering cardiac pacing therapy, said method comprising:

during delivery of a first cardiac pacing scheme, providing three-dimensional position information, for at least two points in time of a cardiac cycle, for an electrode located at a first position in a cardiac space and determining a first local estimator for the electrode at the first position, wherein the first local estimator is a volume derived from the position information of the electrode at the first position;

during delivery of a second cardiac pacing scheme, providing three-dimensional position information, for at least two points in time of a cardiac cycle, for an electrode located at a second position in a cardiac space and determining a second local estimator for the electrode at the second position, wherein the second local estimator is a volume derived from the position information of the electrode at the second position;

comparing the first local estimator with the second local estimator to identify which of the first pacing scheme or the second pacing scheme results in the greater volume; and selecting the identified first or second cardiac pacing scheme as the pacing scheme for delivering a cardiac pacing therapy.

12. A system to select a position for an electrode for delivering a cardiac pacing therapy, said system comprising: one or more processors; memory; and control logic, implemented at least in part by the one or more processors and the memory, configured to: determine a first local estimator for an electrode adapted to be located at a first position in a cardiac space, wherein the first local estimator is a volume derived from three-dimensional information, for at least two points in time of a cardiac cycle, for the electrode adapted to be located at the first position in a cardiac space; determine a second local estimator for an electrode adapted to be located at a second position in a cardiac space, wherein the second local estimator is a volume derived from three-dimensional information, for at least two points in time of a cardiac cycle, for the electrode adapted to be located at the second position in a cardiac space; compare the first local estimator with the second local estimator to identify which of the first position or the second position has the greater volume; and select the identified first position or the second position as the position for the electrode for delivering cardiac pacing therapy.

13. A method for selecting a position for an implantable lead having at least two spaced-apart electrodes for delivering cardiac pacing therapy, said method comprising:
providing three-dimensional position information, for at least two points in time of a cardiac cycle, for at least two spaced-apart electrodes located in a first region of a cardiac space and determining a first regional estimator wherein the first regional estimator defines a volume between the two electrodes and is derived from the position information of the at least two electrodes located at the first region;
providing three-dimensional position information, for at least two points in time of a cardiac cycle, for at least two spaced-apart electrodes located in a second region of the cardiac space and determining a second regional estimator wherein the second regional estimator defines a volume between the two electrodes and is derived from the position information of the at least two electrodes located at the second region;
comparing the first regional estimator with the second regional estimator to identify which of the first region or second region has the greater volume; and
selecting the identified first region or the second region as the position for the at least two spaced-apart electrodes for delivering cardiac pacing therapy.

14. The method of claim 13 wherein the first regional estimator is derived by sweeping a surface between a trajectory path of a first of the at least two spaced-apart electrodes in the first region and a trajectory path of a second of the at least two spaced-apart electrodes in the first region, and the second regional estimator is derived by sweeping a surface between a trajectory path of a first of the at least two spaced-apart electrodes in the second region and a trajectory path of a second of the at least two spaced-apart electrodes in the second region.

15. The method of claim 13 wherein the first regional estimator is derived by extruding a plane defined by a trajectory path of a first of the at least two spaced-apart electrodes in the first region to another plane defined by a trajectory path of a second of the at least two spaced-apart electrodes in the first region, and the second regional estimator is derived by extruding a plane defined by a trajectory path of a first of the at least two spaced-apart electrodes in the second region to another plane defined by a trajectory path of a second of the at least two spaced-apart electrodes in the second region.

16. The method of claim 13 wherein the first regional estimator is derived by connecting the positions of the at least two spaced-apart electrodes in the first region at a plurality of like time points and computing a volume bounded by the series of connected positions, and the second regional estimator is derived by connecting the positions of the at least two spaced-apart electrodes in the second region at a plurality of like time points and computing a volume bounded by the series of connected positions.

17. The method of claim 13 wherein the at least two points in time comprise an end diastolic time and an end systolic time.

18. The method of claim 13 further comprising diagnosing, based at least in part on the first regional estimator and the second regional estimator, a cardiac condition wherein the cardiac condition comprises a condition selected from a group consisting of ischemia, tissue viability, scarring, dyssynchrony and dilated cardiomyopathy.

19. A method for selecting a pacing scheme for delivering cardiac pacing therapy, said method comprising:
during delivery of a first cardiac pacing scheme, providing three-dimensional position information, for at least two points in time of a cardiac cycle, for at least two spaced-apart electrodes located in a first region of a cardiac space and determining a first regional estimator wherein the first regional estimator defines a volume between the two electrodes and is derived from the position information of the at least two electrodes located at the first region;
during delivery of a second cardiac pacing scheme, providing three-dimensional position information, for at least two points in time of a cardiac cycle, for at least two spaced-apart electrodes located in a second region of a cardiac space and determining a second regional estimator wherein the second regional estimator defines a volume between the two electrodes and is derived from the position information of the at least two electrodes located at the second region;
comparing the first regional estimator with the second regional estimator to identify which of the first pacing scheme or second pacing scheme has the greater volume; and
selecting the identified first or second cardiac pacing scheme as the pacing scheme for delivering a cardiac pacing therapy.

20. A system to select a position for an implantable lead having at least two spaced-apart electrodes for delivering cardiac pacing therapy, said system comprising: one or more processors; memory, and control logic, implemented at least in part by the one or more processors and the memory, configured to: determine a first local estimator for two spaced-apart electrodes adapted to be located at a first position in a cardiac space, wherein the first local estimator is a volume derived from three-dimensional information, for at least two points in time of a cardiac cycle, for the two spaced-apart electrodes adapted to be located at the first position in a cardiac space; determine a second local estimator for two spaced-apart electrodes adapted to be located at a second position in a cardiac space, wherein the second local estimator is a volume derived from three-dimensional information, for at least two points in time of a cardiac cycle, for the two spaced-apart electrodes adapted to be located at the second position in a cardiac space; compare the first local estimator with the second local estimator to identify which of the first position or the second position has the greater volume; and select the identified first position or the second position as the position for the at least two spaced-apart electrodes for delivering cardiac pacing therapy.

21. A method comprising:
for each of a plurality of electrode configurations:
delivering cardiac pacing using the electrode configuration;

for a first point in time of a cardiac cycle, providing three-dimensional position information for a first electrode located in a vein of a wall of the left ventricle and for a second electrode located along a wall disposed between the left ventricle and the right ventricle, and determining a first global estimator based on the position information of the first electrode and the second electrode, wherein the first global estimator corresponds to a left ventricular volume at the first point in time;

for a second point in time of the cardiac cycle, providing three-dimensional position information for the first electrode and the second electrode, and determining a second global estimator based on the position information of the first electrode and the second electrode, wherein the second global estimator corresponds to a left ventricular volume at the second point in time; and processing one or both of the first global estimator and the second global estimator to obtain a parameter indicative of cardiac output;

selecting the electrode configuration for delivering a cardiac pacing therapy that optimizes cardiac output.

22. The method of claim 21 wherein the first point in time corresponds to an end diastolic time and the second point in time corresponds to an end systolic time.

23. The method of claim 22 wherein the selecting an electrode configuration comprises selecting an electrode configuration that optimizes cardiac output by maximizing ejection fraction.

24. The method of claim 21 further comprising defining segments between the electrodes wherein segments join the electrodes at a point in time.

25. The method of claim 24 wherein the determining a first global estimator and the determining a second global estimator each determines the respective global estimator based at least in part on the segments.

26. The method of claim 24 further comprising defining segments between the electrodes wherein some segments join the electrodes at an end diastolic point in time and wherein other segments join the electrodes at an end systolic point in time.

27. The method of claim 21 further comprising determining a global estimator differential as a differential between the first global estimator and the second global estimator, the global estimator differential corresponding to a difference in volume of a left ventricle at an end systolic time and at an end diastolic time.

28. A system comprising: one or more processors; memory, and control logic, implemented at least in part by the one or more processors and the memory, configured to: for each of a plurality of electrode configurations: deliver cardiac pacing using the electrode configuration; for a first point in time, of a cardiac cycle, provide three-dimesional position information for a first electrode adapted to be located in a vein of a wall of a left ventricle and for a second electrode adapted to be located along a wall disposed between the left ventricle and a right ventricle, and determine a first global estimator based on position information of the first electrode and the second electrode, wherein the first global estimator corresponds to a left ventricular volume at the first point in time; for a second point in time of the cardiac cycle, provide three-dimensional position information for the first electrode and the second electrode, and determine a second global estimator based on the position information of the first electrode and the second electrode, wherein the second global estimator corresponds to a left ventricular volume at the second point in time; and process one or both of the first global estimator and the second global estimator to obtain a parameter indicative of cardiac output; and select the electrode configuration for delivering a cardiac pacing therapy that optimizes cardiac output.

* * * * *